US007520854B2

(12) United States Patent
Sato

(10) Patent No.: US 7,520,854 B2

(45) Date of Patent: Apr. 21, 2009

(54) ENDOSCOPE SYSTEM ALLOWING MOVEMENT OF A DISPLAY IMAGE

(75) Inventor: Saichi Sato, Sagamihara (JP)

(73) Assignee: Olympus Corporation (JP)

(*) Notice: Subject to any disclaimer, the term of this patent is extended or adjusted under 35 U.S.C. 154(b) by 697 days.

(21) Appl. No.: 11/052,422

(22) Filed: Feb. 7, 2005

(65) Prior Publication Data

US 2006/0015012 A1 Jan. 19, 2006

(30) Foreign Application Priority Data

Jul. 14, 2004 (JP) ............................ 2004-207700

(51) Int. Cl.
*A61B 1/045* (2006.01)
*A61B 1/005* (2006.01)

(52) U.S. Cl. ....................... 600/118; 600/146; 600/152; 348/65; 348/74

(58) Field of Classification Search ................. 600/109, 600/118, 146, 152, 173; 348/65, 74
See application file for complete search history.

(56) References Cited

U.S. PATENT DOCUMENTS

| | | | | |
|---|---|---|---|---|
| 5,153,721 | A * | 10/1992 | Eino et al. | 382/152 |
| 5,627,584 | A * | 5/1997 | Nishikori et al. | 348/72 |
| 5,836,869 | A * | 11/1998 | Kudo et al. | 600/173 |
| 6,241,657 | B1 * | 6/2001 | Chen et al. | 600/117 |
| 6,663,559 | B2 * | 12/2003 | Hale et al. | 600/118 |
| 2002/0175992 | A1 * | 11/2002 | Eino | 348/65 |
| 2003/0078475 | A1 * | 4/2003 | Hirata et al. | 600/152 |
| 2004/0225185 | A1 * | 11/2004 | Obata et al. | 600/118 |
| 2005/0197536 | A1 * | 9/2005 | Banik et al. | 600/179 |

FOREIGN PATENT DOCUMENTS

| | | |
|---|---|---|
| JP | 08-029703 | 2/1996 |
| JP | 2000-287921 | 10/2000 |
| JP | 2001-000390 | 1/2001 |
| JP | 2001-167272 | 6/2001 |
| JP | 2001-258819 | 9/2001 |
| JP | 2001-350104 | 12/2001 |
| JP | 2002-345745 | 12/2002 |

* cited by examiner

*Primary Examiner*—John P Leubecker
(74) *Attorney, Agent, or Firm*—Ostrolenk, Faber, Gerb & Soffen, LLP

(57) ABSTRACT

Rotate instructing switches 26, 27, and 28 of an operating remote controller 5 are pressed and then a CPU 12 controls image processing of an image pickup processing portion 8, a direction calculation processing portion 10, and a rotating-image processing portion 9 in accordance with an operating signal to rotate and display a screen 21 displayed on a screen of an LCD 4A. Touch-panel type direction instructing portions arranged on the LCD 4A are operated, thereby supplying operating signals to the CPU 12 via a touch panel controller 4*a*. The CPU 12 determines, by using a determining area table arranged in a ROM 13 based on the operating signal, which direction instructing portion is pressed. Simultaneously, the CPU 12 calculates the moving direction and the amount of movement of an image by a direction processing portion 11 and the direction calculation processing portion 10, and controls the driving of a driving unit 7 based on a calculated result.

16 Claims, 18 Drawing Sheets

1
4: DISPLAY UNIT
5: OPERATING REMOTE CONTROLLER
4A
MONITOR
OPERATING PORTION 5A
5B
ROTATION INSTRUCTING PORTION
2
3a: INSERTING PORTION
3
9
IMAGE PICKUP PROCESSING PORTION 8
ROTATING-IMAGE PROCESSING PORTION
3b: CCD
CONTROL PORTION
12
7: DRIVING UNIT
DIRECTION CALCULATION PROCESSING PORTION 10
7A
11
INSERTING-PORTION DRIVING CIRCUIT
DIRECTION PROCESSING PORTION
6: SYSTEM CONTROL UNIT

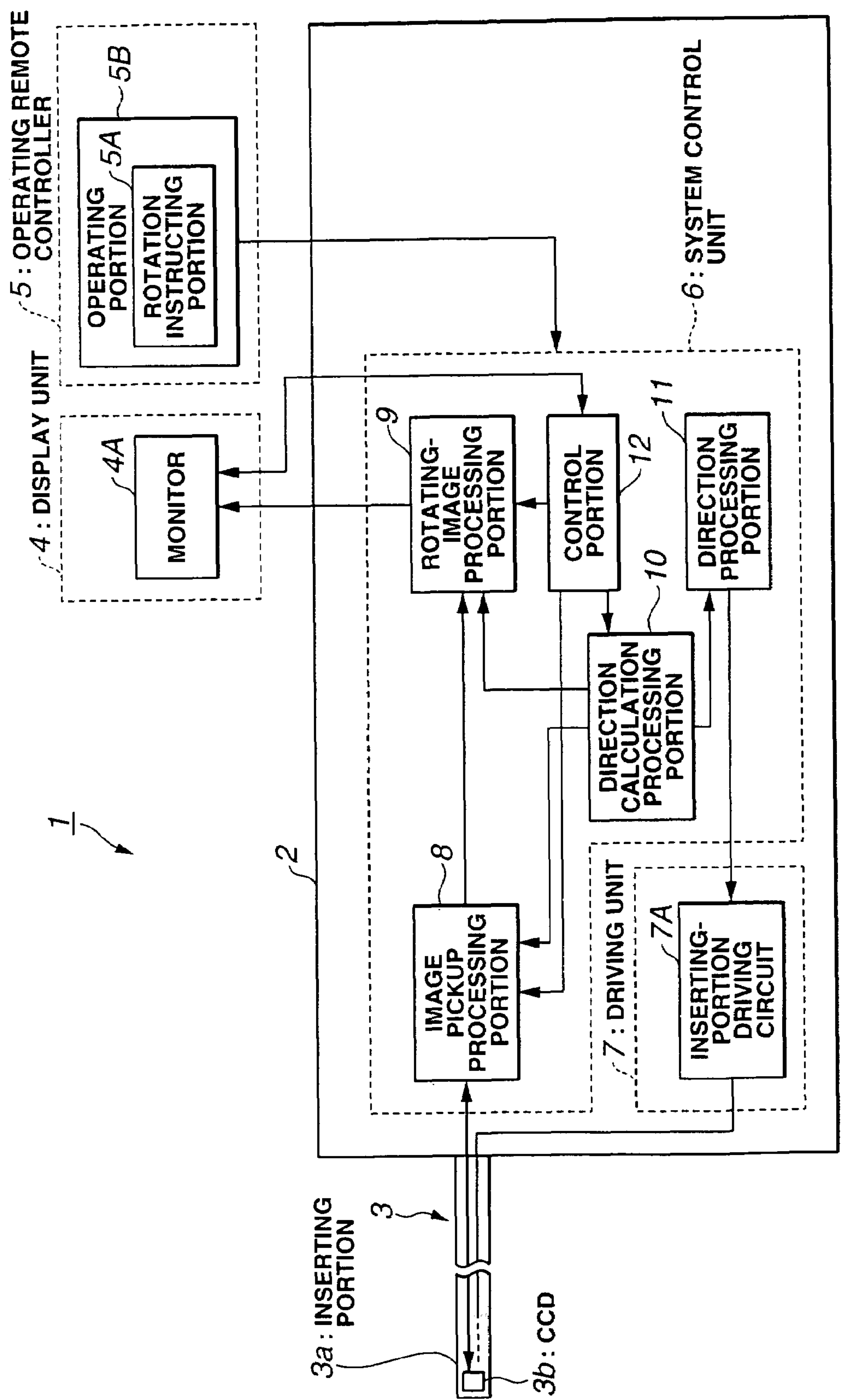
FIG.1
1
5 : OPERATING REMOTE CONTROLLER
OPERATING PORTION
5B
5A
ROTATION INSTRUCTING PORTION
4 : DISPLAY UNIT
4A
MONITOR
6 : SYSTEM CONTROL UNIT
9
ROTATING-IMAGE PROCESSING PORTION
CONTROL PORTION
12
11
DIRECTION PROCESSING PORTION
10
DIRECTION CALCULATION PROCESSING PORTION
2
8
IMAGE PICKUP PROCESSING PORTION
7 : DRIVING UNIT
7A
INSERTING-PORTION DRIVING CIRCUIT
3
3a : INSERTING PORTION
3b : CCD 1
2
2a
2b
2c
2d
2e
2f
3
3a : INSERTING PORTION
3b : CCD
4
4A
LCD
5
5B
5C
5a(5A)
5b
5c
5d
CPU
RS232 I/F
6
8a
CCU
8b
A/D
8c
JPEG PROCESSING CIRCUIT
8d
SWITCHING CIRCUIT
8e
RAM
9a
SUPER-IMPOSING CIRCUIT
9b
D/A
12
CPU
13
ROM
14
VRAM
15
RS232 I/F
4a
TOUCH PANEL CONTROLLER
16
RAM
17
RS232 I/F
18
ATA I/F
19
USB I/F
20
7(7A)
7a
RS232 I/F
7b
CPU
7c
M FIG.4C
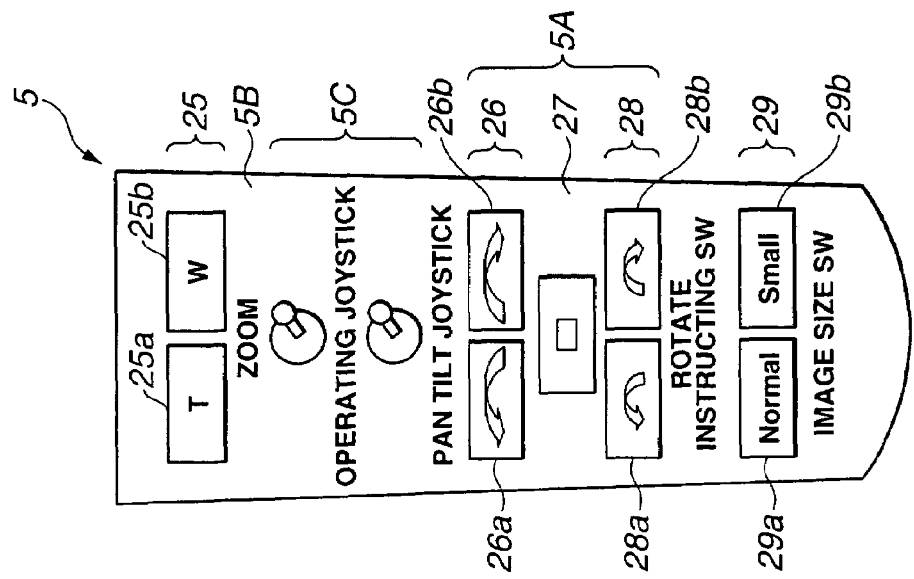
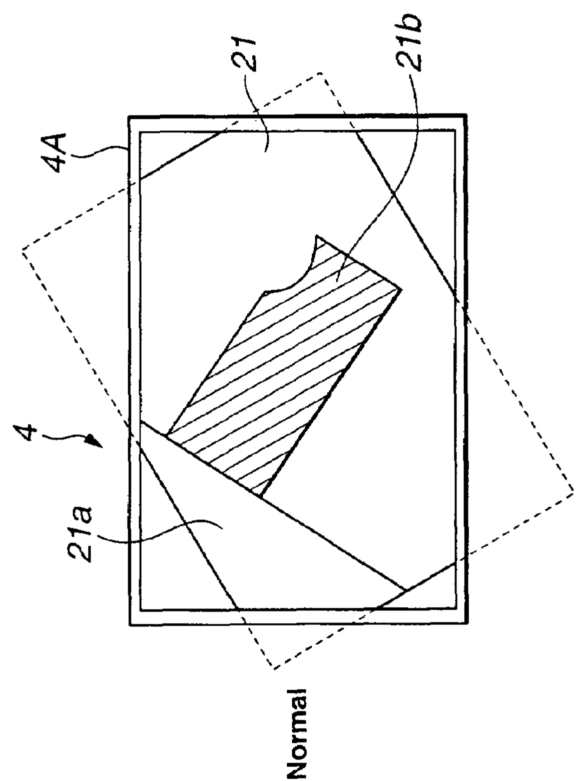
FIG.4A
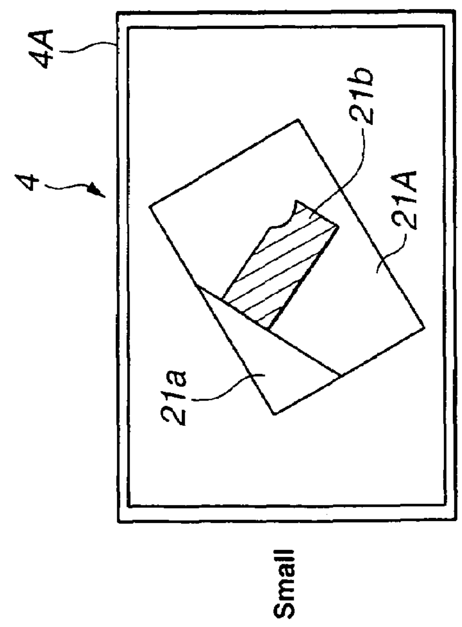
FIG.4B ROTATE TO RIGHT
LARGE
LARGE
SMALL
21
21a
21b ROTATE TO LEFT
LARGE
LARGE
SMALL
21
21a
21b RETURN IMAGE POSITION
RETURN
21
21a
21b 5
ZOOM
PAN·TILT
OPERATION
5C
30
21a
21b
ZOOM
31A
31B
31C
31D
31E
31F
31G
31H
31
A
B
C
D
E
F
G
H

FIG.8

DETERMINING AREA TABLE

| CONTROL AREA / ROTATING-ANGLE AREA | AREA 1 | AREA 2 | AREA 3 | AREA 4 | AREA 5 | AREA 6 | AREA 7 | AREA 8 |
|---|---|---|---|---|---|---|---|---|
| AREA 1 | U | UL | L | DL | D | DR | R | UP |
| AREA 2 | UR | U | UL | L | DL | D | DR | R |
| AREA 3 | R | UR | U | UL | L | DL | D | DR |
| AREA 4 | DR | R | UR | U | UL | L | DL | D |
| AREA 5 | D | DR | R | UR | U | UL | L | DL |
| AREA 6 | DL | D | DR | R | UR | U | UL | L |
| AREA 7 | L | DL | D | DR | R | UR | U | UL |
| AREA 8 | UL | L | DL | D | DR | R | UR | U |

U : UP D : DOWN R : RIGHT L : LEFT
UR : UPPER RIGHT UL : UPPER LEFT DR : DOWN RIGHT DL : DOWN LEFT

FIG.10
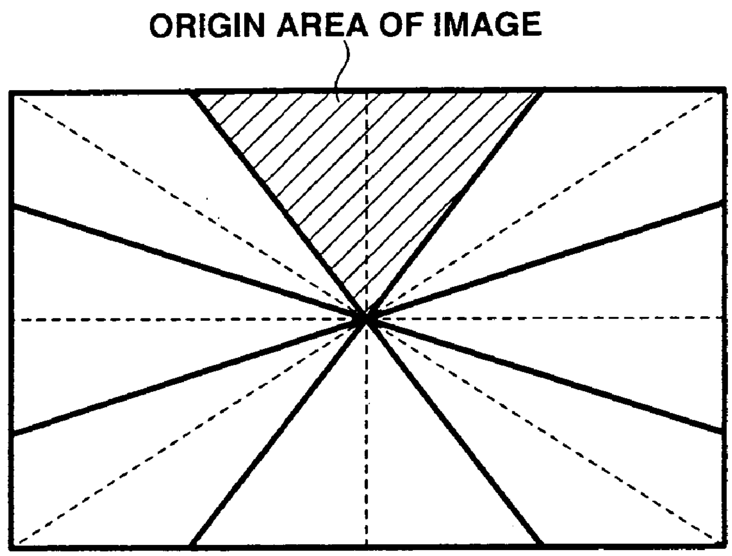
INITIAL IMAGE WITHOUT ROTATING INSTRUCTION
INSTRUCT ROTATE
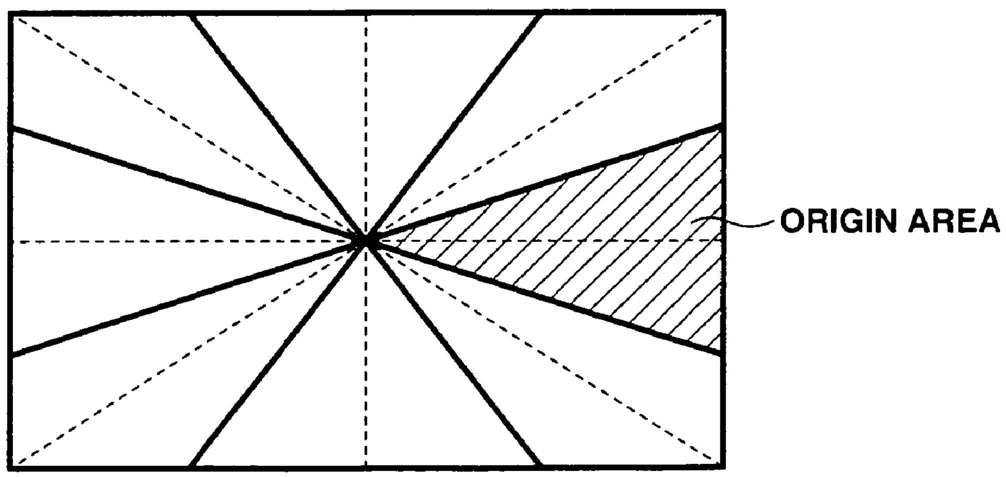
CURRENT DISPLAY IMAGE
(INSTRUCTED TO ROTATE TO RIGHT IN 80°)

5
5C
OPERATE INSERTING MEANS
31A
31B
31C
31D
31E
31F
31G
31H
31
21a
21b
A
B
C
D
E
F
G
H

1A(1B)
3a : INSERTING PORTION
3b : CCD
LCD
CPU
RS232 I/F
D/A
SUPER-IMPOSING CIRCUIT
SWITCHING CIRCUIT
A/D
CCU
RAM
JPEG PROCESSING CIRCUIT
ROM
VRAM
TOUCH PANEL CONTROLLER
USB I/F
ATA I/F
CONTROL SIGNAL
IMAGE SIGNAL
RECORDING MEDIUM
M

1A(1B)
2
6A(6B)
3
3a : INSERTING PORTION
3b : CCD
2a
CCU
8a
A/D
8b
RAM
8e
SWITCHING CIRCUIT
8d
IMAGE PROCESSING CIRCUIT
8c1
SUPER-IMPOSING CIRCUIT
9a
ROM
13
VRAM
14
TOUCH PANEL CONTROLLER
4a
D/A
9b
RS232 I/F
15
20
RAM
16
CPU
12
RS232 I/F
17
ATA I/F
18
USB I/F
19
7(7A)
RS232 I/F
7a
CPU
7b
M
7c
4
4A
LCD
2f
2b
2c
2d
2e
5
5a(5A)
5b
CPU
5c
RS232 I/F
5d
5C
5B
32A
32B
32
CONTROL SIGNAL
IMAGE SIGNAL
RECORDING MEDIUM
35

ENDOSCOPE SYSTEM ALLOWING MOVEMENT OF A DISPLAY IMAGE

This Application claims benefit of Japanese Patent Application No. 2003-200156 filed in Japan on Jul. 22, 2003, and No. 2004-207700 filed in Japan on Jul. 14, 2004, the contents of which are incorporated by this reference.

BACKGROUND OF THE INVENTION

1. Field of the Invention

The present invention relates to an endoscope device having an image pickup processing portion which converts an observed image into an image signal to be displayed on a display unit of an endoscope for obtaining the observed image by inserting an inserting portion at a portion to be observed. More particularly, the present invention relates to an endoscope device which displays a preferable observed image to be displayed without any feeling of strangeness in accordance with a field-of-view direction of an operator, irrespective of the setting direction of the display unit.

2. Description of the Related Art

Recently, an endoscope is widely used in the medical field and the industrial field. Generally, an observed image obtained by the endoscope is displayed on a display unit.

The above-mentioned endoscope device performs the examination and medical procedure by inserting an inserting portion of the endoscope while observing the observed image (endoscope image) displayed on the display unit such as a monitor. Therefore, it is requested that an operator performs the examination and medical procedure without any feeling of strangeness and the desired observed image is certainly displayed for recognition.

In consideration of the above-mentioned request, for example, Japanese Unexamined Patent Application Publication No. 2001-350104, Japanese Unexamined Patent Application Publication No. 2001-390, and Japanese Unexamined Patent Application Publication No. 2000-287921 disclose the endoscope devices as conventional arts.

SUMMARY OF THE INVENTION

According to the present invention, an endoscope device comprises: an endoscope that can be inserted to a portion to be observed and has an inserting portion having image pickup means at the distal-end side thereof that obtains an observed image; an image pickup processing portion that converts the observed image of the endoscope into an image signal that can be displayed on a display unit; a direction instructing portion that instructs a moving direction of a display image displayed on the display hand unit; and a direction calculation processing portion that processes the amount of movement of the display image in accordance with an instruction from the direction instructing portion.

Further, an endoscope device according to the present invention comprises: an image pickup processing portion that converts an observed image obtained by image pickup means of an endoscope inserted to a portion to be observed, into an image signal that can be displayed on a display unit; a direction instructing portion that instructs a moving direction of a display image displayed on the display hand unit; and a direction calculation processing portion that processes the amount of movement of the display image in accordance with an instruction from the direction instructing portion.

BRIEF DESCRIPTION OF THE DRAWINGS

FIG. 1 is a diagram showing the structure of the entire system of an endoscope device of an endoscope according to a first embodiment of the present invention.

FIG. 4A is an explanatory diagram showing a display example when the observed image is in the normal mode.

FIG. 4B is an explanatory diagram showing a display example when the observed image is in the small mode.

FIG. 4C is a diagram showing the structure of the operating remote controller for switching a display mode.

FIG. 8 is an explanatory diagram showing the contents of a determining area table arranged in a control unit.

FIG. 10 is an explanatory diagram for determining a rotating area of an image upon instructing the right rotation in an angle of 80° from no instruction of rotation.

DESCRIPTION OF THE PREFERRED EMBODIMENTS

Figure 2:
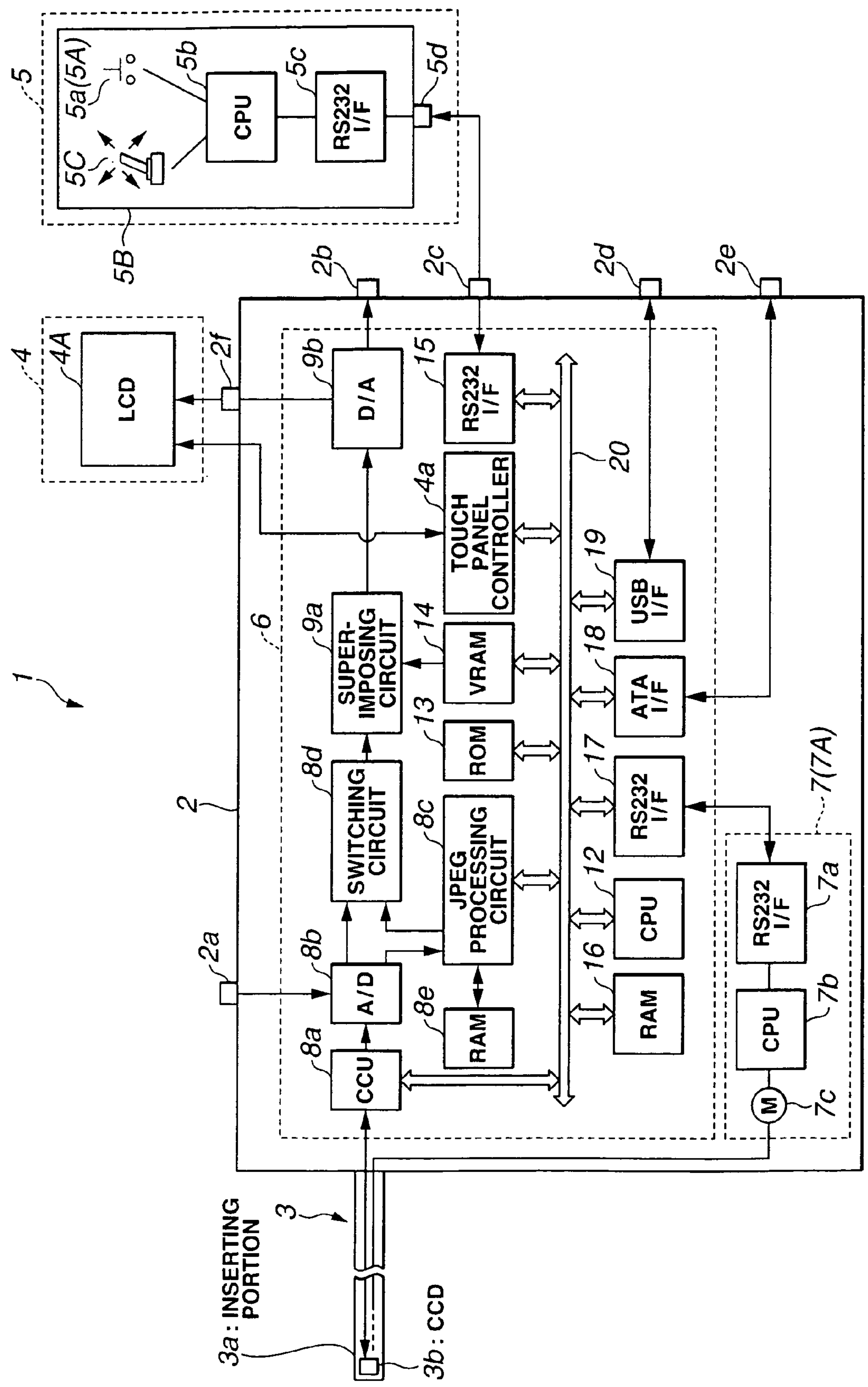
FIG. 2 is a block diagram showing a specific electric circuit structure of the endoscope device shown in FIG. 1.

Hereinbelow, a description will be given of embodiments of the present invention with reference to the drawings.

FIGS. 1 to 12 show an endoscope device according to a first embodiment of the present invention.

Referring to FIG. 1, an endoscope device 1 according to the first embodiment is suitable to the industrial application, and comprises: a device main body 2; an endoscope 3 that is connected to the device main body 2 and is used for endoscope examination; a display unit 4 that displays the observed image from the endoscope 3; and an operating remote controller 5 that is connected to the device main body 2 and instructs various operations such as the bending operation of the endoscope 3 and display instruction of the display unit 4.

The endoscope 3 comprises an inserting portion 3*a* that is inserted into the portion to be observed. The inner portion on the distal-end side of the inserting portion 3*a* comprises a CCD (solid-state image pickup device) 3*b*. Although not shown, the inserting portion on the distal-end side comprises: an observing optical system that captures the observed image to the CCD 3*b* and an optical system that irradiates the portion to be observed with light from a light guide which is inserted in the inserting portion 3*a*. Although not shown, the light guide is connected to a light source device arranged in the device main body 2 at the rear end side of the light guide. Further, the inserting portion 3*a* comprises a bending portion which can freely be bent in the vertical and horizontal directions at the distal-end side of the inserting portion 3*a*. The driving of the bending portion is controlled on the device main body 2 side.

The endoscope 3 supplies a picked-up image of the observed portion picked-up by the CCD 3*b* to an image pickup processing portion 8 in the device main body 2 via a signal line (not shown) arranged in the inserting portion 3*a*.

The device main body 2 mainly comprises: a system control unit 6 that controls the entire operations; and a driving unit 7 that drives a bending portion (not shown) of the endoscope 3. The driving unit 7 comprises an inserting-portion driving circuit 7A including driving means that drives the bending portion (not shown) of the endoscope. The inserting-portion driving circuit 7A is controlled by a control portion 12 of the system control unit 6, which will be described later. The system control unit 6 comprises: the image pickup processing portion 8 that receives the observed image from the endoscope 3; a rotating-image processing portion 9 that receives an output signal of the image pickup processing portion 8; a direction calculation processing portion 10 which supplies a result of direction calculating processing to the image pickup processing portion 8 and a direction processing portion 11; the direction processing portion 11 connected to the direction calculation processing portion 10; and the control portion 12 that controls the driving of the driving unit 7 and various processing of the image pickup processing unit 8, the rotating-image processing portion 9, the direction calculation processing portion 10, and the direction processing portion 11.

The image pickup processing portion 8 performs predetermined signal processing of the received observed image for conversion, and supplies the converted signal to the rotating-image processing portion 9. When the operating remote controller 5 performs the operation for instructing the image rotation, the rotating-image processing portion 9 performs predetermined image rotating processing of the image signal under the control of the control portion 12. Then, the rotating-image processing portion 9 outputs the processed signal to a monitor 4A. On the other hand, if image rotation is not instructed, the image signal is outputted to the monitor 4A without any processing.

The direction calculation processing portion 10 corrects the bending direction and the image moving direction from the rotating angle of the current image based on an instruction for rotating the image and an instruction moving the image by the operating remote controller 5 under the control of the control portion 12. Further, the direction calculation processing portion 10 supplies the result of calculation to the image pickup processing portion 8, the rotating-image processing portion 9, and the direction processing portion 11. A detailed operation of the direction calculation processing portion 10 and the control portion 12 will be described later.

The direction processing portion 11 obtains the direction based on an operating instruction from the operating remote controller 5 and a result of calculation of the direction calculation processing portion 10, creates a control signal for bending the bending portion (not shown) of the endoscope 3 in the obtained direction, and supplies the created control signal to the driving unit 7. Therefore, the inserting-portion driving circuit 7A of the driving unit 7 drives the bending portion (not shown) of the endoscope 3 to be bent in the direction based on the supplied control signal.

The direction processing portion 11 determines the amount of motion of the driving unit 7 in the bending direction, and the original information includes a joystick angle of an operating portion 5B and a bending direction corrected from the rotating angle of the current image by the direction calculation processing portion 10. In the PAN/TILT operation of the image pickup processing portion 8, the PAN/TILT joystick angle of the operating portion 5B and the PAN/TILT direction corrected from the rotating angle of the current image by the direction calculation processing portion 10 are outputted to the image pickup processing portion 8.

The control portion 12 is electrically connected to a rotation instructing portion 5A and the operating portion 5B of the operating remote controller 5. The control portion 12 controls the processing of the rotating-image processing portion 9, the direction calculation processing portion 10, and the image pickup processing portion 8 based on the operating signals. That is, upon supplying the operating signal by the operating portion 5B, the control portion 12 controls the driving of the bending portion (not shown) and the image pickup processing portion 8 so as to execute various operations indicated by the operating signal, e.g., bending operation of the endoscope 3, the enlargement/reduction and brightness of the display image and operation for changing the image size.

When the operating signal is supplied by the rotation instructing portion 5A, the control portion 12 controls the rotating-image processing portion 9 to execute the processing for rotating the display image displayed on the monitor 4A based on the operating signal in this case.

Next, a detailed description is given of a specific electric circuit structure of the endoscope device according to the first embodiment with reference to FIG. 2.

Referring to FIG. 2, the system control unit 6 comprises: a camera control unit (hereinafter, abbreviated to a CCU) 8*a*; an A/D converter 8*b*; a JPEG processing circuit 8*c*; a switching circuit 8*d*; a RAM 8*e*; a superimposing circuit 9*a*; a D/A converter 9*b*; a ROM 13; a VRAM 14; RS232 I/Fs 15 and 17;

a CPU 12; a RAM 16; an ATA I/F 18; a USB I/F 19; a touch panel controller 4*a;* and a bus 20 that connects the circuits.

The CCU 8*a* amplifies the image pickup signal sent from the CCD 3*b,* performs video processing for converting the amplified signal into an image signal by dividing it into a luminance signal and color signals, and outputs the processed signal to the A/D converter 8*b,* and zooms an output signal, performs the PAN/TILT in the zoom, and adjusts the brightness of image based on the control signal outputted from the CPU 12.

The A/D converter 8*b* converts the output signal of the CCU 8*a* (analog image signal) into digital image data, and supplies the obtained digital image data to the switching circuit 8*d* and the JPEG processing circuit 8*c*. An image signal from another external device can be supplied to the A/D converter 8*b* via an external input terminal 2*a*.

In the case of setting a compression processing mode by the CPU 12, the JPEG processing circuit 8*c* compresses the supplied digital image data and outputs the compressed data to the bus 20. In the case of setting a decompression processing mode by the CPU 12, the JPEG processing circuit 8*c* performs complex processing of the compressed image data read from an image recording medium (not shown) connected to a terminal 2*e* via the ATA I/F 18, and outputs the processed signal to the switching circuit 8*d*.

In this case, the CPU 12 enables the JPEG processing circuit 8*c* to execute the processing on the work area of the RAM 8*e*. The compressed image data is temporarily stored in the RAM 16 via the bus 20. The CPU 12 controls the recording and reading of the image data to/from the RAM 16, and the remote controller records the image data to another image recording medium (not shown) via the ATA I/F 18.

In the case of setting a non-compression processing mode by the CPU 12, the JPEG processing circuit 8*c* outputs the supplied image data to the bus 20 without compression, and outputs, to the switching circuit 8*d,* the non-compressed image data read from the other image recording medium (not shown) connected to the terminal 2*e* via the ATA I/F 18.

The switching circuit 8*d* appropriately switches the digital image data from the A/D converter 8*b* and the compressed digital image data from the JPEG processing circuit 8*c,* and outputs the switched data to the superimposing circuit 9*a*.

The VRAM 14 temporarily stores the image data decompressed by the CPU 12 or graphic data such as a menu created by the CPU 12.

The superimposing circuit 9*a* superimposes the digital image data outputted from the switching circuit 8*d* and the graphic data or decompressed image data outputted from the VRAM 14 under the control of the CPU 12, and supplies the superimposed digital image data to the D/A converter 9*b*.

The D/A converter 9*b* converts the output signal (digital image data) of the superimposing circuit 9*a* to an analog image signal, and outputs the obtained image signal to an LCD 4A serving as a monitor via an output terminal 2*f.* As mentioned above, the LCD 4A displays the image based on the image signal. An output image signal of the D/A converter 9*b* is supplied to the external output terminal 2*b,* and is outputted and displayed on external display means such as another monitor connected to the external output terminal 2*b*.

Connected to the bus 20 arranged in the system control unit 6 are the CPU 12 for controlling operations of the entire endoscope device 1, the CCU 8*a,* the JPEG processing circuit 8*c,* the ROM 13, the VRAM 14, the touch panel controller 4*a,* the RS232 I/Fs 15 and 17, the RAM 16, the ATA I/F 18, and the USB I/F 19.

The CPU 12 is operated on the program stored in the ROM 13. In the CPU 12, the image data serving as the compressed data obtained via the bus 20 from the JPEG processing circuit 8*c* is subjected to the image decompression, image rotation, and image re-compression in the RAM 16, then, is outputted to the JPEG processing circuit 8*c,* and is further outputted to the switching circuit 8*d.* The image data serving as the non-compressing data is subjected to the image rotation in the RAM 16, then, is outputted to the JPEG processing circuit 8*c,* and is outputted to the switching circuit 8*d.*

In the CPU 12, the image data serving as compressed data obtained via the bus 20 from the JPEG processing circuit 8*c* is subjected to the image decompression and image rotation in the RAM 16, and is outputted to the VRAM 14. The image data serving as the non-compressed data is subjected to the image rotation, and is outputted to the VRAM 14.

The RS232 I/Fs 15 and 17 are interfaces which receive and send the signals such as a control command from the CPU 12 or another CPU 5*b* or 7*b*. The RS232 I/F 15 is connected to an RS232 I/F 5*c* of the operating remote controller 5 via an input/output terminal 2*c*. The RS232 I/F 17 is connected to an RS232 I/F 7*a* of the driving unit 7.

The CPU 12 captures an operating signal from the operating remote controller 5 via the RS232 I/F 15, and controls the corresponding block circuit based on the operating signal. For example, when the operating signal controls the bending portion (not shown) of the endoscope 3, the CPU 12 recognizes the operating signal and supplies the control signal via the RS232 I/F 17 to the RS232 I/F 7*a* of the driving unit 7. The driving unit 7*a* captures the control signal to the CPU 7*b* via the RS232 I/F 7*a*. The CPU 7*b* controls the driving of a motor 7*c* based on the control signal. Thus, the bending portion (not shown) of the endoscope 3 is driven in the bending state based on the operating signal.

The ATA I/F 18 is an interface which receives and sends the digital image data to/from an image recording medium such as a PC card connected to via the input/output terminal 2*e* (not shown). The CPU 12 controls the storage and reading operation of the image data to the recording medium (not shown) via the ATA I/F 18.

The USB I/F 19 is an interface which receives and sends the control signal or receives and sends the digital image data to/from another external device such as another external device such as personal computer under the control of the CPU 12.

Referring to FIG. 2, the device main body 2 having the system control unit 6 comprises: an external input terminal 2*a* connected to the A/D converter 8*b;* an output terminal 2*f* that supplies an output signal of the D/A converter 9*b* to the LCD 4A; an external output terminal 2*b* that outputs an output signal of the D/A converter 9*b* to external display means; an input terminal 2*c* that captures the operating signal from the operating remote controller 5 to the RS232 I/F 15; a connecting terminal 2*d* that is connected to an external device such as a personal computer via a USB I/F; and the input/output terminal 2*e* that captures the digital image data from an external recording medium (not shown) such as a PC card via the ATA I/F 18 and writes the captures image data.

Referring to FIG. 2, the operating remote controller 5 operated by the operator has the operating portion 5B having switches. The operating portion 5B comprises: switches 5*a* including a rotation instructing portion 5A serving as the feature according to the first embodiment; a joystick 5C comprising a PAN/TILT joystick in the zoom operation and a joystick for operating the bending operation; the CPU 5*b* for converting the operating signals from the switches 5*a* and the joystick 5C into the control signals and controlling the output; an RSA232 I/F 5*c* for sending the control signals from the CPU 5*b* to the system control unit 6 of the device main body 2; and an output terminal 5*d* connected to the RSA232 I/F 5*c*.

Figure 3A:
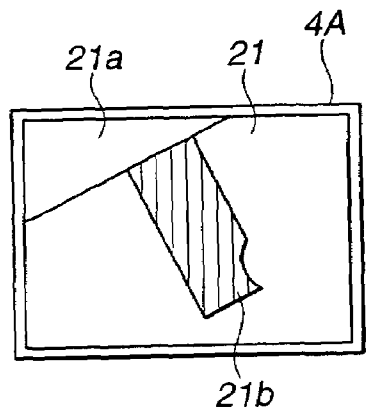
FIG. 3A is an explanatory diagram showing a display example of an observed image displayed on a display unit.
Figure 3B:
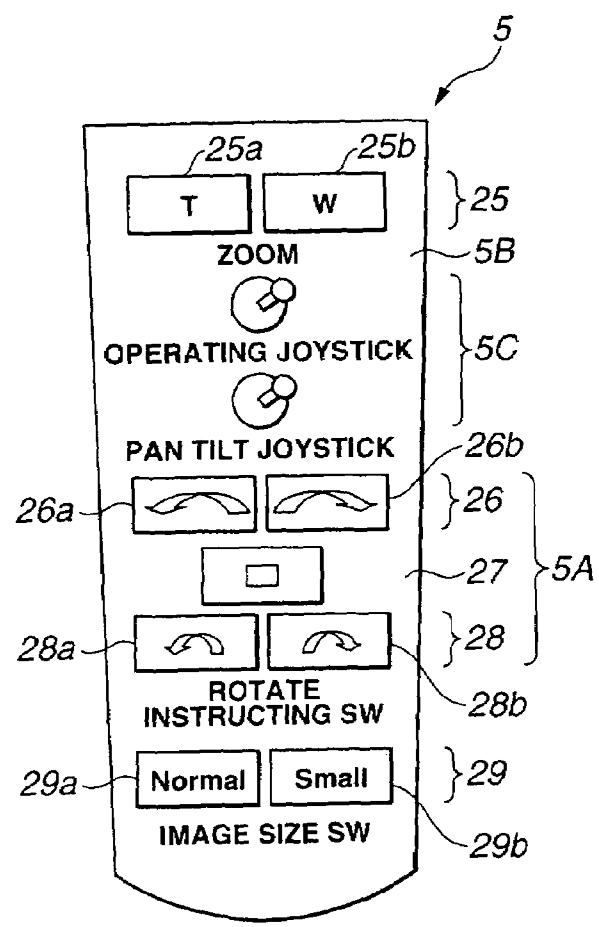
FIG. 3B is a structure diagram showing a structure example of an operating remote controller.

Referring to FIG. 3(*b*), as the actual appearance, the operating remote controller 5 comprises: a zoom switch 25; the joystick 5C; rotate instructing switches 26, 27, and 28 serving as the rotation instructing portion 5A; and an image size switch 29, from the top side of the operating portion 5B (remote controller main body).

The zoom switch 25 comprises: a TELE button 25*a* for enlarging (zooming-up) the display image; and a WIDE button 25*b* for reducing (zooming-down) the display image.

The joystick 5C can instruct the operating directions serving as any direction, e.g., up, down, left, or right direction by one projected stick, and comprises an operating switch for bending the bending portion of the endoscope 3 in the inclining direction of the stick and an operating switch for the PAN/TILT operation of the image in the zoom operation.

The image size switch 29 comprises a normal switch 29*a* for displaying the image on the screen of the LCD 4A with a predetermined size and a small switch 29*b* for displaying the image on the screen of the LCD 4A with a reducing image size by a predetermined reducing ratio.

The rotate instructing switches 26, 27, and 28 serving as the rotation instructing portions 5A are operating switches which rotate the display image at an arbitrary angle so that the direction of the display image displayed on the LCD 4A matches a viewing direction of the operator.

Referring to FIG. 3(*b*), the rotate instructing switches comprise the large-rotate instructing switch 26, the reference-angle switch 27, and the small-rotate instructing switch 28.

The large-rotate instructing switch 26 comprises: a left-rotate instructing switch 26*a* for rotating the display image counterclockwise in a predetermined large angle; and a right-rotate instructing switch 26*b* for rotating the display image clockwise in a predetermined large angle.

The small-rotate instructing switch 28 comprises: a left-rotate instructing switch 28*a* for rotating the display image counterclockwise in a predetermined small angle; and a right-rotate instructing switch 28*b* for rotating the display image clockwise in a predetermined small angle.

The reference-angle switch 27 is a switch for returning the display image to a predetermined reference angle.

In addition, although not shown, the operating portion 5B of the operating remote controller 5 has menu buttons for adjusting the brightness of image, recording the image, and setting various operations. The menu buttons are pressed, thereby setting the various operations.

According to the first embodiment, the large-rotate instructing switch 26 or the small-rotate instructing switch 28 is pressed, thereby rotating the display image counterclockwise/clockwise in a predetermined angle. However, the present invention is not limited to this. The rotation of image display may be set every predetermined angle by continuous pressing operation. That is, the large-rotate instructing switch 26 is continuously pressed, thereby continuously rotating the display image counterclockwise/clockwise in every predetermined large angle. The small-rotate instructing switch 28 is continuously pressed, thereby continuously rotating the display image counterclockwise/clockwise in every predetermined small angle.

The above-mentioned predetermined angle can arbitrarily be set by the operator. If a predetermined angle serving as the large-rotation instruction is 20° and a predetermined angle serving as the small-rotation instruction is 2°, it is excessively advantageous for the operator to observe the display image fast at a desired angle.

FIG. 3(*a*) shows a display example for displaying the observed image on the LCD 4A. For example, when the inserting portion of the endoscope 3 is inserted in a jet engine and the periphery of a turbine blade 21*b* arranged on a rotor 21*a* is examined as the portion to be observed by inserting the inserting portion of the endoscope 3 in a jet engine. Then, in the endoscope device 1 according to the first embodiment, the screen of the LCD 4A displays an endoscope image 21 for picking-up the periphery of the rotor 21*a* and the turbine blade 21*b*.

In this case, the operator appropriately presses the rotate instructing switches 26, 27, and 28 of the operating remote controller 5. Then, the CPU 12 controls the rotating-image processing portion 9 in response to the pressing operation and thus the endoscope image 21 displayed on the screen of the LCD 4A can be moved by right rotation shown in FIG. 5(*a*), by left rotation shown in FIG. 5(*b*), or by return to the reference angle shown in FIG. 5(*c*). A detail description will be given of the operation of the detailed display control later.

In the endoscope device 1 according to the first embodiment, the image processing of the image display enables the image to be rotated and displayed at the operator's desired angle and further enables the display operation on the monitor so that the endoscope image from the endoscope matches the viewing direction of the operator.

Figure 7A:
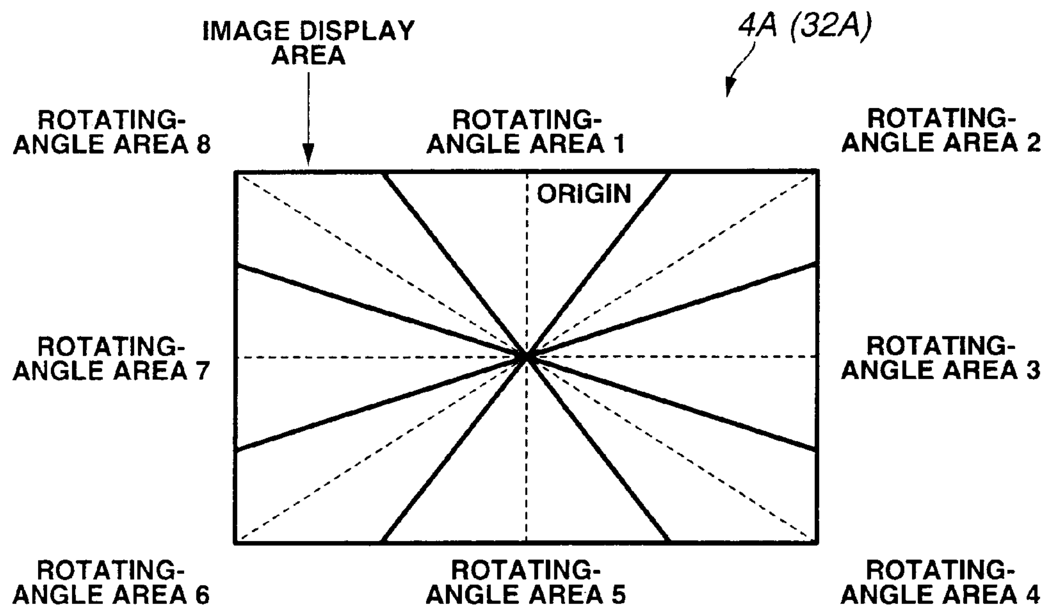
FIG. 7A is an explanatory diagram of an image display area for determining a rotating area and a control area, and of an image display area for determining a rotating angle and a rotating area.
Figure 7B:
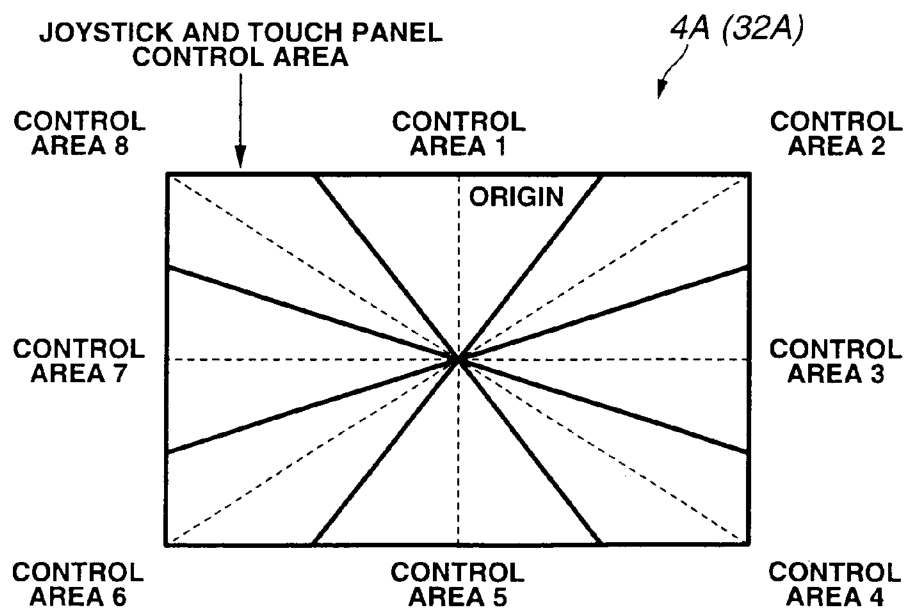
FIG. 7B is an explanatory diagram showing a joystick and a touch panel control area.

Specifically, referring to FIG. 7(*b*), at a predetermined position on the screen of the LCD 4A, eight direction instructing portions are arranged, including an upper left direction (control area 8), an up direction (control area 1), an upper right direction (control area 2), a left direction (control area 7), a right direction (control area 3), a down left direction (control area 6), a down direction (control area 5), and a down left direction (control area 4). The direction instructing portions are operated by touch-panel systems. Further, the direction instructing portions may be hardware switches corresponding to the control areas.

That is, referring to FIG. 2, the direction instructing portions of the LCD 4A are electrically connected to the touch panel controller 4*a* connected to the bus 20. The touch panel controller 4*a* receives the operating controls operated by the direction instructing portions on the screen of the LCD 4A and supplies the operating signals to the CPU 12.

The CPU 12 determines, based on the operating signal, by using a determining area table shown in FIG. 8 arranged in the ROM 13, which direction instructing portion is pressed. Simultaneously, the CPU 12 corrects the bending direction from the rotation instructing angle of the image by using the direction calculation processing portion 10, calculates the image moving direction and the amount of image movement, and outputs the calculated result to the direction processing portion 11. The direction processing portion 11 converts the calculated result of the direction calculation processing portion 10 into a command for controlling the driving unit 7 and controls the driving of the driving unit 7, thereby bending the bending portion of the endoscope 3 so as to display, on the LCD 4A, the image in the direction corresponding to the direction instructing portion of the operator. That is, the bending operation of the bending portion of the endoscope 3 is executed in association with the touch operation of any direction instructing portion on the LCD 4A of the operator.

The CPU 12 determines based on the operating signal by using the determining area table shown in FIG. 8 arranged in the ROM 13, which direction instructing portion is pressed. Simultaneously, the CPU 12 corrects the PAN/TILT direction from the rotation instructing angle of the zoomed image by using the direction calculation processing portion 10, calculates the image moving direction and the amount of image movement, and outputs the calculated result to the image pickup processing portion 8.

The image pickup processing portion 8 performs the PANS/TILTS operation on the zoomed image so as to display the image in the direction corresponding to the direction instructing portion of the operator on the LCD 4A based on the calculated result of the direction calculation processing portion 10.

That is, the PAN/TILT operation of the zoomed image is executed in accordance with the touch operation of any direction instructing portion on the LCD 4A of the operator.

Further, the operator presses the small switch 29*b* of the operating remote controller 5 and thus the CPU 12 decompresses the image captured as JPEG. Furthermore, the CPU 12 displays the endoscope image 21 with the image size reduced by a predetermined reducing ratio on the screen of the LCD 4A so as to enclose the entire observed image on the screen of the LCD 4A in the case of rotation. Then, the operator presses the normal switch 29*a* of the operating remote controller 5 and thus the CPU 12 controls the image pickup processing portion 8. Referring to FIG. 4(*a*), the screen 21 with a predetermined size (e.g., predetermined size that is initialized: refer to FIG. 3(*a*)) is displayed on the screen.

Next, a detailed description is given of a control operation example serving as the feature of the endoscope device 1 according to the first embodiment with reference to FIGS. 1 to 12.

Now, the power of the endoscope device 1 shown in FIG. 1 is turned on, thereby entering an available state. The inserting portion 3*a* of the endoscope 3 is inserted in the jet engine, thereby examining the periphery of the turbine blade (refer to FIG. 3(*a*)). In this case, the CPU 12 in the system control unit 6 reads a necessary program from the ROM 13, thereby controlling the entire system. For example, a processing flow shown in FIG. 12 starts. That is, in step S1, the CPU 12 determines whether or not the PAN/TILT joystick 5C of the operating remote controller 5 instructs the operation. If NO in step S1, the processing shifts to step S3.

If the operator instructs the PAN/TILT operation, the processing shifts to step S2. In step S2, by using a shaded portion on the top in FIG. 10 of an initial image without any rotating instruction, a shaded portion on the bottom in FIG. 10 of the origin area of the image that is rotation-instructed and is currently displayed is compared with an image display area in FIG. 7(*a*) to be determined as which rotating-angle area an origin area of the image.

The location of the operated PAN/TILT switch is compared with the joystick and touch panel control areas shown in FIG. 7(*b*) to determine which control area.

Figure 9:
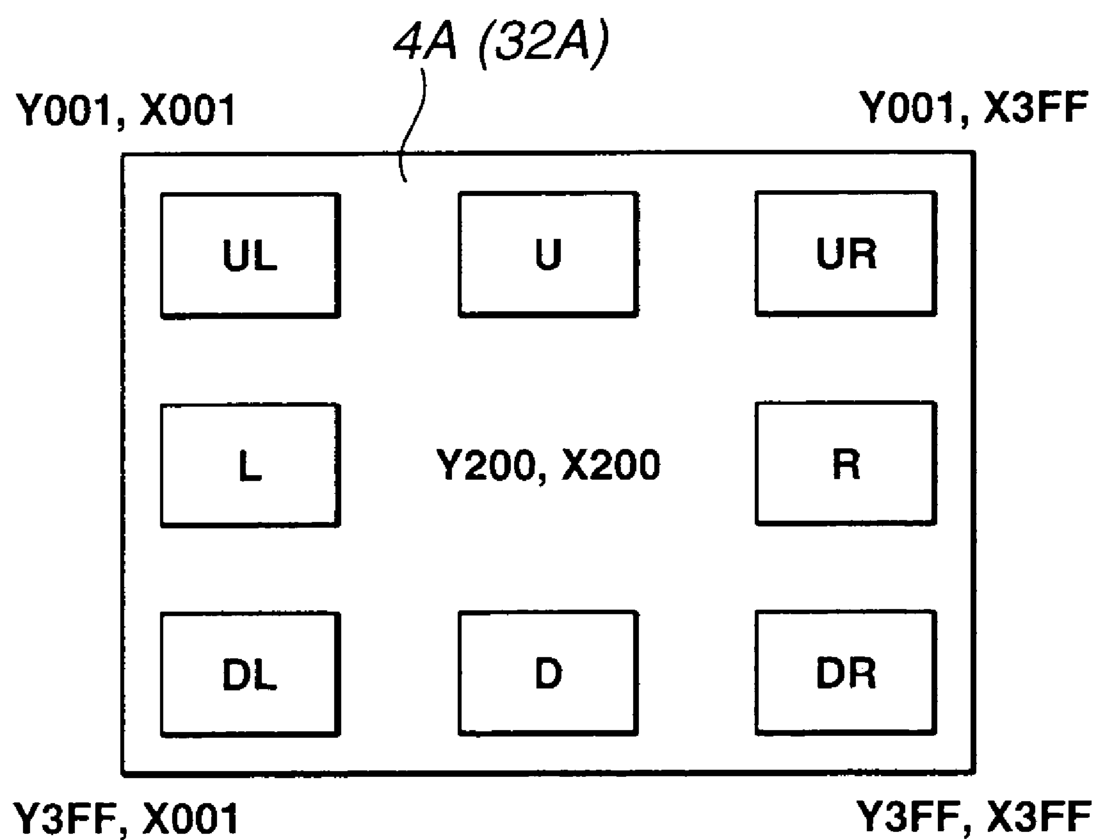
FIG. 9 is an explanatory diagram showing an image moving direction corresponding to an image display area of the display unit.

Based on the determining table shown in FIG. 8, the coordinate instruction shown in FIG. 9 of the PAN/TILT coordinate is outputted to the image pickup processing portion 8.

The image pickup processing portion 8 performs the PANS/TILTS operation on the image in response to the coordinate instruction.

Figure 6:
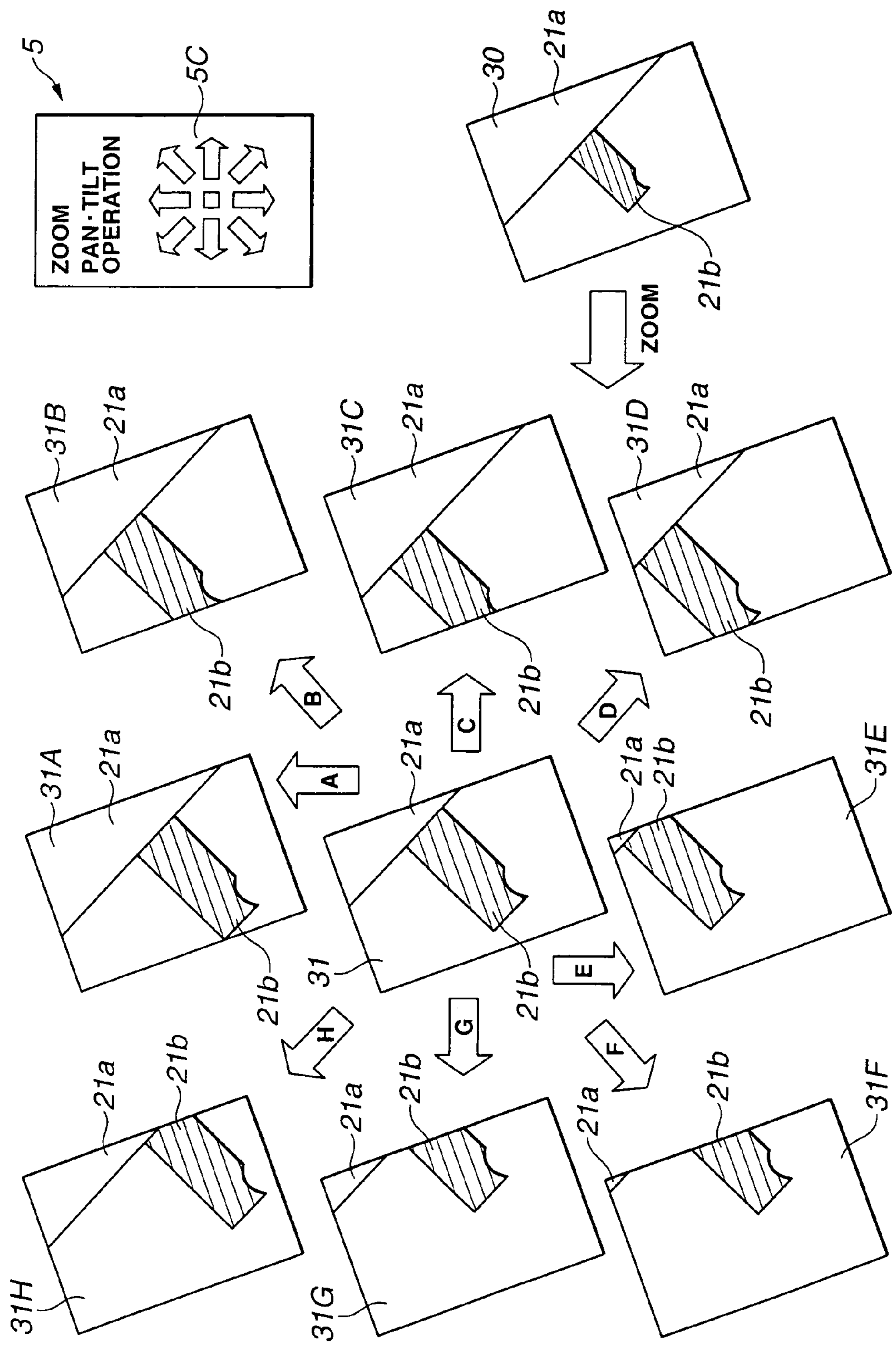
FIG. 6 is an explanatory diagram of the display operation in the PAN/TILT operation in image processing without interlocking with the bending operation.

FIG. 6 shows a display example of the PAN/TILT operation.

In the display example shown in FIG. 6 of PAN/TILT operation, the image inputted by the image pickup processing portion 8 is rotated in an angle of 80° in response to the right instruction. In this case, the origin of the image in the image display area shown in FIG. 7(*a*) is determined as the rotating area 3. In the case of selecting the operation in an arrow direction (A) shown in FIG. 6, the image is determined as the control area 1 from the joystick and touch panel control area shown in FIG. 7(*b*). The operation is determined as "R" direction based on the determining area table shown in FIG. 8. The coordinate instruction of "R" direction on the PAN/TILT coordinate shown in FIG. 9 is outputted to the image pickup processing portion 8. The image inputted from the CCD 3*b* is moved to an image (31A) shown in FIG. 6 in the "R" direction.

In step S3, it is determined by the CPU 12 whether or not the joystick 5C of the operating remote controller 5 instructs the operation. If NO in step S3, the processing shifts to step S5.

If the operator instructs the operation of the joystick 5C of the operating remote controller 5, the processing shifts to step S4. In step S4, the image origin is compared with the image display area shown in FIG. 7(*a*) to determine which rotating-angle area the image origin is.

It is determined which control area is the operated operating joystick by the comparison with the joystick and touch panel control area shown in FIG. 7(*b*).

Based on the determining table shown in FIG. 8, the coordinate instruction of the coordinates shown in FIG. 9 of driving the bending portion of the inserting portion is outputted to the inserting-portion driving circuit 7A.

The inserting-portion driving portion 7A operates the bending portion (not shown) in the "R" direction in response to the coordinate instruction.

Figure 11:
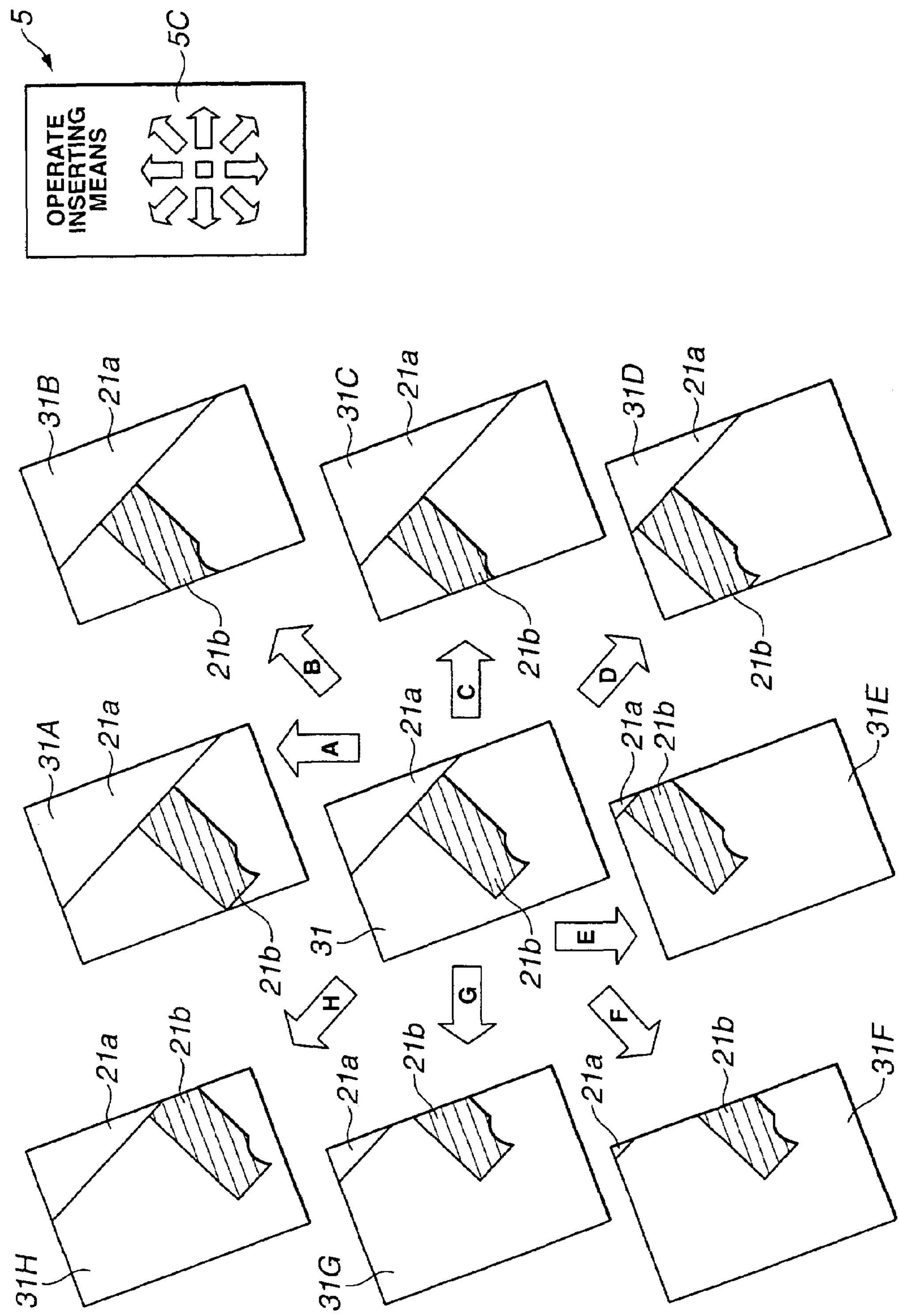
FIG. 11 is an explanatory diagram showing a display example of an image upon instructing the right rotation in an angle of 80° with the joystick.
Figure 12:
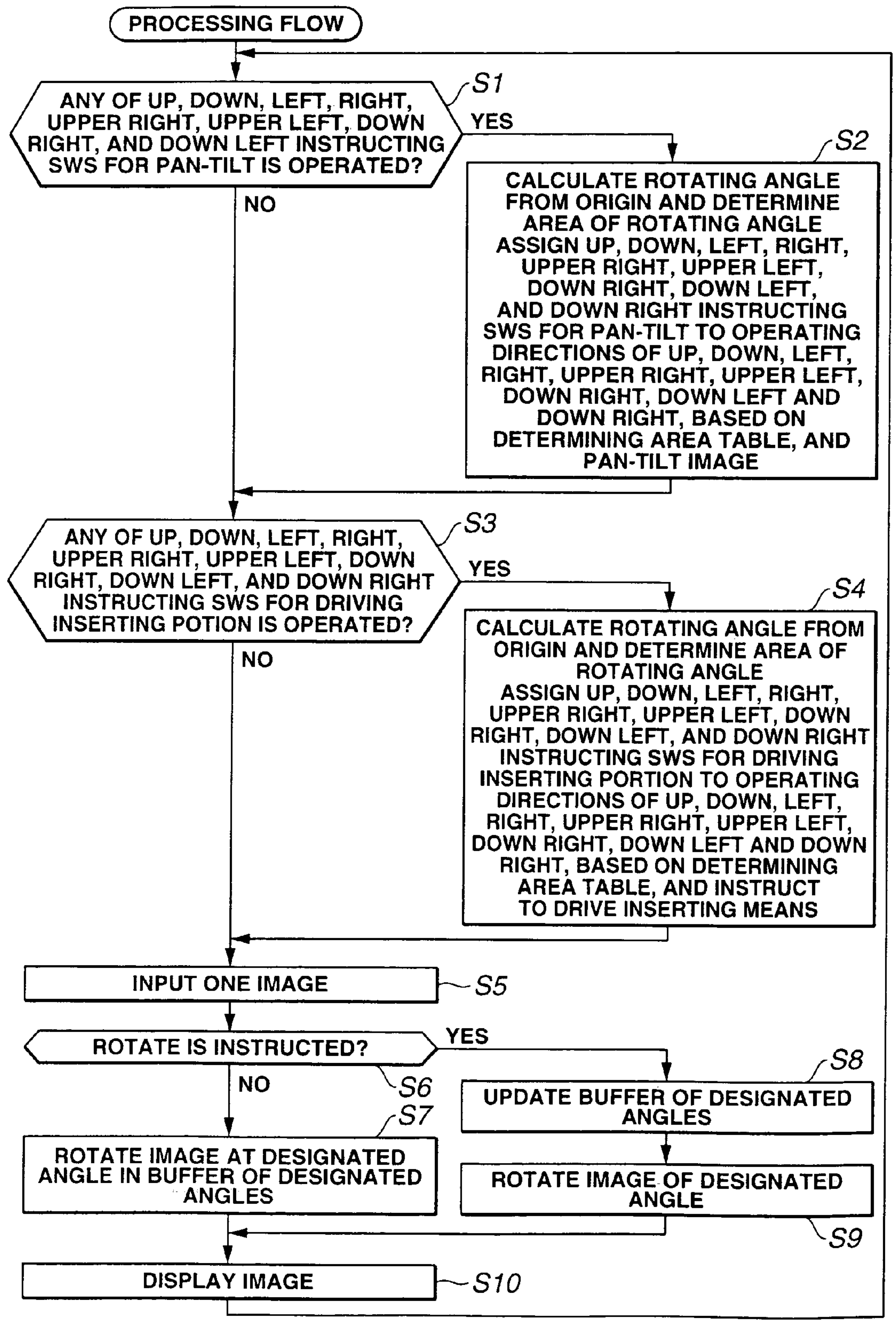
FIG. 12 is a flowchart showing a control example of the control unit according to the first embodiment.

In a display example shown in FIG. 11 operated by the operating joystick, the image inputted by the image pickup processing portion 8 is rotated clockwise in an 80°-degree arc in response to the instruction of right rotation.

In this case, the origin of image in the image display area shown in FIG. 7(*a*) is determined as the rotating area 3. In the case of selecting the operation in an arrow (A) direction shown in FIG. 11, the operation is determined as "R" direction based on the determining area table shown in FIG. 8. The coordinate instruction of "R" direction on the coordinates for driving the bending portion of the inserting portion is outputted to the inserting-portion driving unit 7A.

The inserting-portion driving unit 7A operates the bending portion (not shown) in the "R" direction in response to the coordinate instruction.

In the processing in step S5, the image data having one image is captured in the rotating-image processing portion 9 and the processing shifts to determination in step S6.

In the determination in step S6, it is determined in the CPU 12 whether or not the operator instructs the rotation of image by the rotate instructing switch 5A (26 to 28) of the operating remote controller 5. In this case, if NO in step S6, in subsequent processing in step S7, the image is rotated at the designated angle in the buffer of designated angles on the RAM (16) shown in FIG. 2 by using the rotating-image processing portion 9. Then, the processing shifts to step S10.

Incidentally, in the processing in step S7, the image may not be rotated in a predetermined angle and this setting may arbitrarily be set.

If the image rotation is instructed in the determination in step S6, the processing in steps S8 and S9 is executed and then the processing shifts to step S10.

If the image rotation is instructed, in step S8, the CPU 12 updates the rotating angle predetermined in step S8 to the designated angle in the buffer of designated angles on the RAM (16) shown in FIG. 2 in accordance with the angle designated by the rotate instructing switch 5A. In subsequent step S9, the CPU 12 rotates the image at the angle designated by the rotate instructing switch 5A (corresponding to the designated angle in the buffer of designated angles) by using the rotating-image processing portion 9 and then the processing shifts to step S10.

Figure 5A:
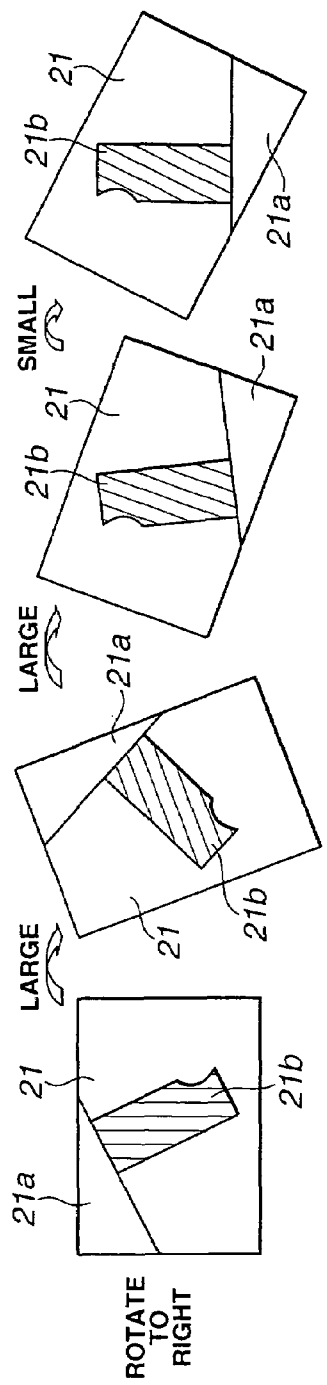
FIG. 5A is an explanatory diagram of a display example of right rotation, as a display example of instructing the rotation.
Figure 5B:
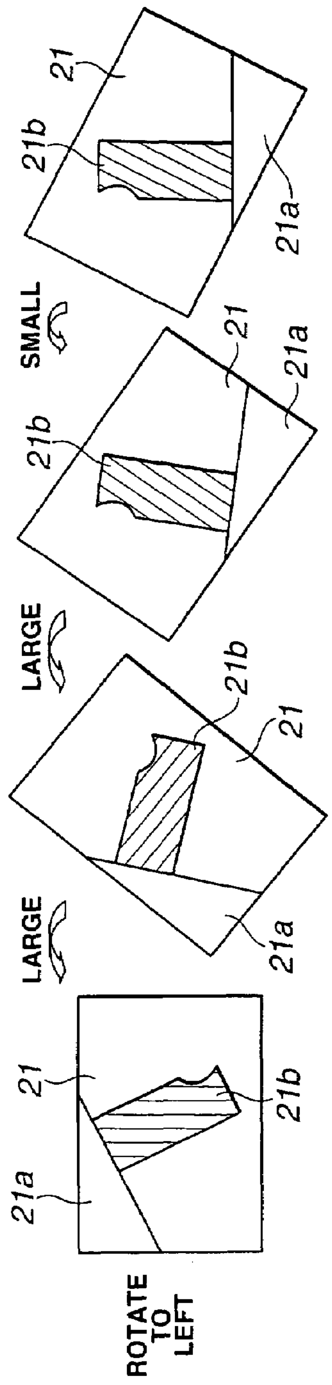
FIG. 5B is an explanatory diagram of a display example of the left rotation.
Figure 5C:
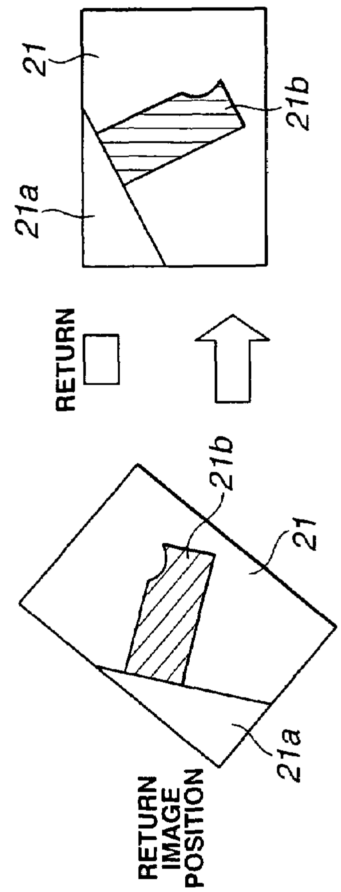
FIG. 5C is an explanatory diagram showing a display example upon returning an image position.

FIG. 5(*a*) shows a display example of the right-rotation instruction of the operator. Referring to FIG. 5(*a*), the operator presses the right large-rotate instructing switch 26*b* shown in FIG. 3(*b*) from the endoscope image 21 shown on the left and then the CPU 12 updates the designated angle in the buffer of designated angles. The CPU 12 rotates the endoscope image 21 clockwise in a predetermined large angle and displays the rotated image. After that, the right large-rotate instructing switch 26*b* is pressed, the CPU 12 updates the designated angle in the buffer of designated angles on the RAM 16 of the RAM shown in FIG. 2, and the CPU 12 rotates the screen clockwise in a predetermined large angle and displays it. Then, the right small-rotate instructing switch 28*b* is pressed, the CPU 12 updates the designated angle in the buffer of designated angles on the RAM 16 shown in FIG. 2, and the CPU 12 rotates the currently-displayed endoscope image 21 clockwise in a predetermined small angle and displays it.

FIG. 5(*b*) shows a display example of the left-rotation instruction of the operator. Referring to FIG. 5(*b*), the operator presses the left large-rotate instructing switch 26*a* shown in FIG. 3(*b*), the CPU 12 updates the designated angle in the buffer of designated angles on the RAM (16) shown in FIG. 2, and the CPU 12 rotates the endoscope image 21 counterclockwise in a predetermined large angle and displays it.

After that, the left small-rotate instructing switch 28*a* is pressed, the CPU 12 updates the designated angle in the buffer of designated angles on the RAM 16 shown in FIG. 2, and the CPU 12 rotates the currently-displayed endoscope image 21 in a predetermined small angle and displays it.

FIG. 5(*c*) shows a display example for pressing the reference switch 27 by the operator. Referring to FIG. 5(*c*), the reference switch 27 is pressed after displaying the image rotated based on the instruction of image rotation, the designated angle in the buffer of designated angles on the RAM 16 shown in FIG. 2 is returned to the origin angle. As shown in FIG. 5(*c*), the CPU 12 returns the endoscope image 21 rotated in a predetermined angle (image processed in step S7) to the first endoscope image 21.

In step S10, the image processed in step S7 or S9 is set to the VRAM 14, it is converted into an analog signal by the D/A 9*b* via the superimposing circuit 9*a*, and it is displayed on the LCD 4A.

After that, the CPU 12 returns the processing to step S1 and then continuously repeats the above-mentioned processing.

According to the first embodiment, the display image displayed on the monitor 4A is rotated in the direction based on the rotation instructed by the rotation instructing portion 5A by the operator under the control of the rotating-image processing portion 9, the direction processing portion 11, the direction calculation processing portion 10, and the CPU 12 for controlling them. Further, the bending operation of the bending portion of the endoscope is controlled in the direction of the operation instructed by the operator and the image in the direction is displayed on the monitor 4A. Therefore, the endoscope image from the endoscope matches that in the viewing direction of the operator without any feeling of strangeness in the examination.

FIGS. 13 to 16 show an endoscope device according to a second embodiment of the present invention.

According to the second embodiment, an endoscope control unit 32 for controlling the entire endoscope device is connected to the endoscope main body. Further, the endoscope control unit 32 includes the main structure blocks including the rotating-image processing portion 9, the direction calculation processing portion 10, and the direction processing portion 11 arranged in the system control unit 6 according to the first embodiment, and controls the processing for rotating and displaying the image serving as the feature of the present invention and the bending operation of the endoscope.

Figure 13A:
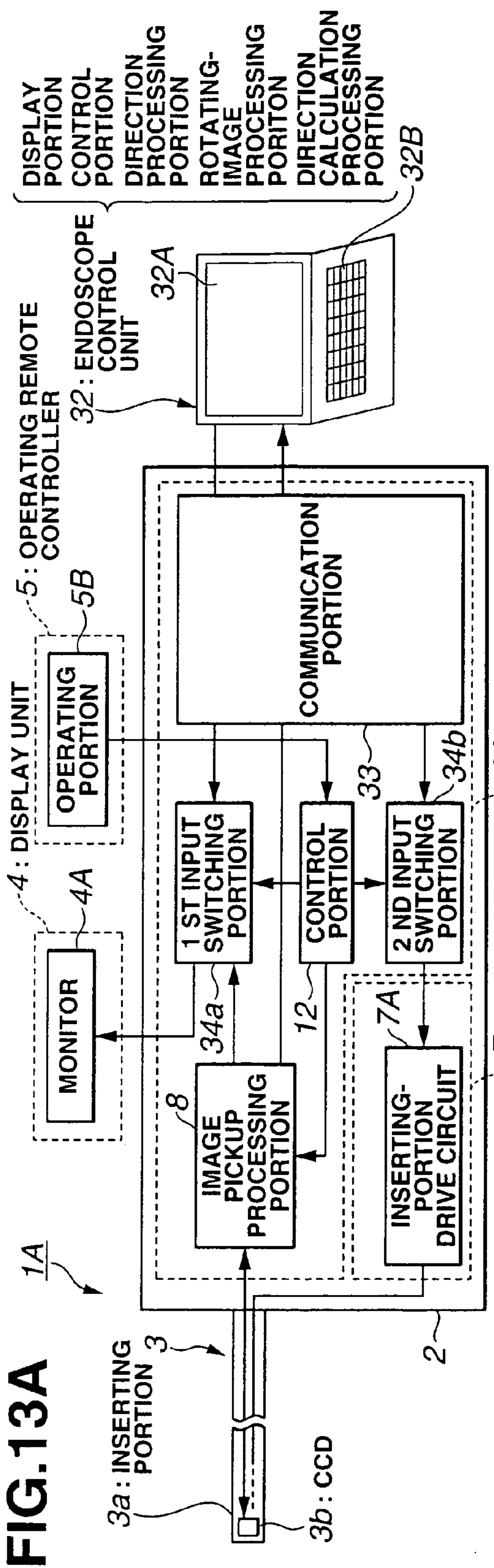
FIG. 13A is a diagram showing the structure of the entire system for switching an image in an endoscope device according to a second embodiment of the present invention.
Figure 13B:
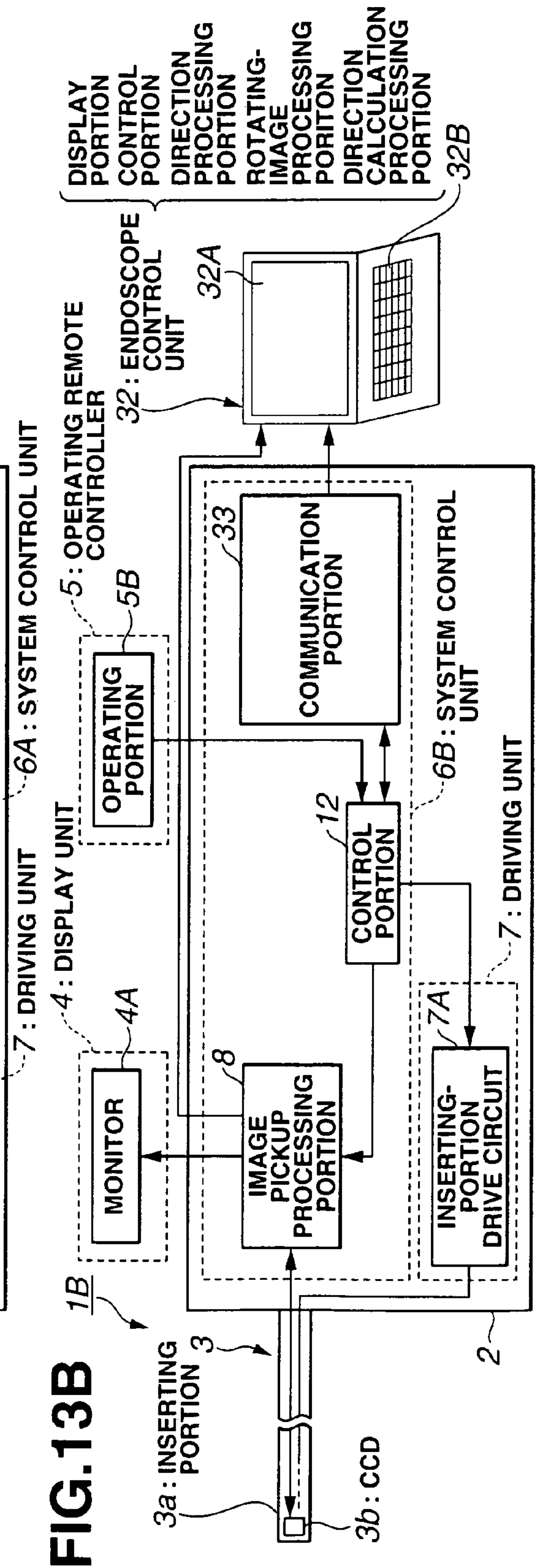
FIG. 13B is a diagram showing the structure of the entire simplified system.

Referring to FIG. 13(*a*), the rotating-image processing portion 9, the direction processing portion 11, and the direction calculation processing portion 10 are deleted from a system control unit 6A in an endoscope device 1A. Further, the system control unit 6A comprises: a first switching portion 34*a* which receives an output signal from the image pickup processing portion 8; a communication portion 33 which is connected to the first switching portion 34*a* and which receives and sends a control signal and sends image data to the endoscope control unit 32; and a second switching portion 34*b* which is connected to the communication portion 33, the control portion 12, and the driving unit 7.

A notebook-type personal computer (hereinafter, referred to as a PC) serving as the endoscope control unit 32 is connected to the communication portion 33. The PC 32 comprises the rotating-image processing portion 9, the direction processing portion 11, and the direction calculation processing portion 10 which are arranged in the system control unit 6 according to the first embodiment as mentioned above. The PC 32 performs the same control operation as that of the system control unit 6 according to the first embodiment.

The communication portion 33 is a communication I/F which receives and sends the endoscope image or image data from the PC 32, or receives and sends various data such as a bending control signal of the endoscope. For example, when the communication portion 33 receives the image data from the PC 32, the communication portion 33 supplies the received image data to the first switching portion 34*a*. When the communication portion 33 receives the bending control signal, the communication portion 33 supplies the received bending control signal to the second switching portion 34*b*.

The first switching portion 34*a* switches the image data from the PC 32 and the image data from the image pickup processing portion 8, and outputs and displays the switched image data on the monitor 4A. That is, according to the second embodiment, the observed image through the endoscope and the image supplied from the PC 32 such as the rotated image processed in accordance with the rotating instruction are arbitrarily switched and displayed.

The second switching portion 34*b* switches a bending control signal from the PC 32 and a bending control signal created based on the operation of the operating remote controller 5 under the switching control of the PC 32, outputs the switched signal to the driving unit 7, and drives the bending portion (not shown) of the endoscope 3. In this case, if the switching operation of the PC 32 is preferentially controlled, the PC 32 can execute the entire control operations. Further, the control portion 12 in the system control unit 6 on the device main body 2 can control the switching operation of the second switching portion 34*b*. That is, according to the second embodiment, the PC 32 can control the bending operation of the bending portion (not shown) of the endoscope 3.

According to the second embodiment, referring to FIG. 13(*b*), the first and second switching units 34*a* and 34*b* arranged in the system control unit 6A may be deleted and a system control unit 6B may be structured so as to supply the image data or bending control signal to the control portion 12 via the communication portion 33. Thus, with the simple structure, the control portion 12 in association with the control operation of the PC 32 side controls various operations, similarly to the system control unit 6A.

Figure 14:
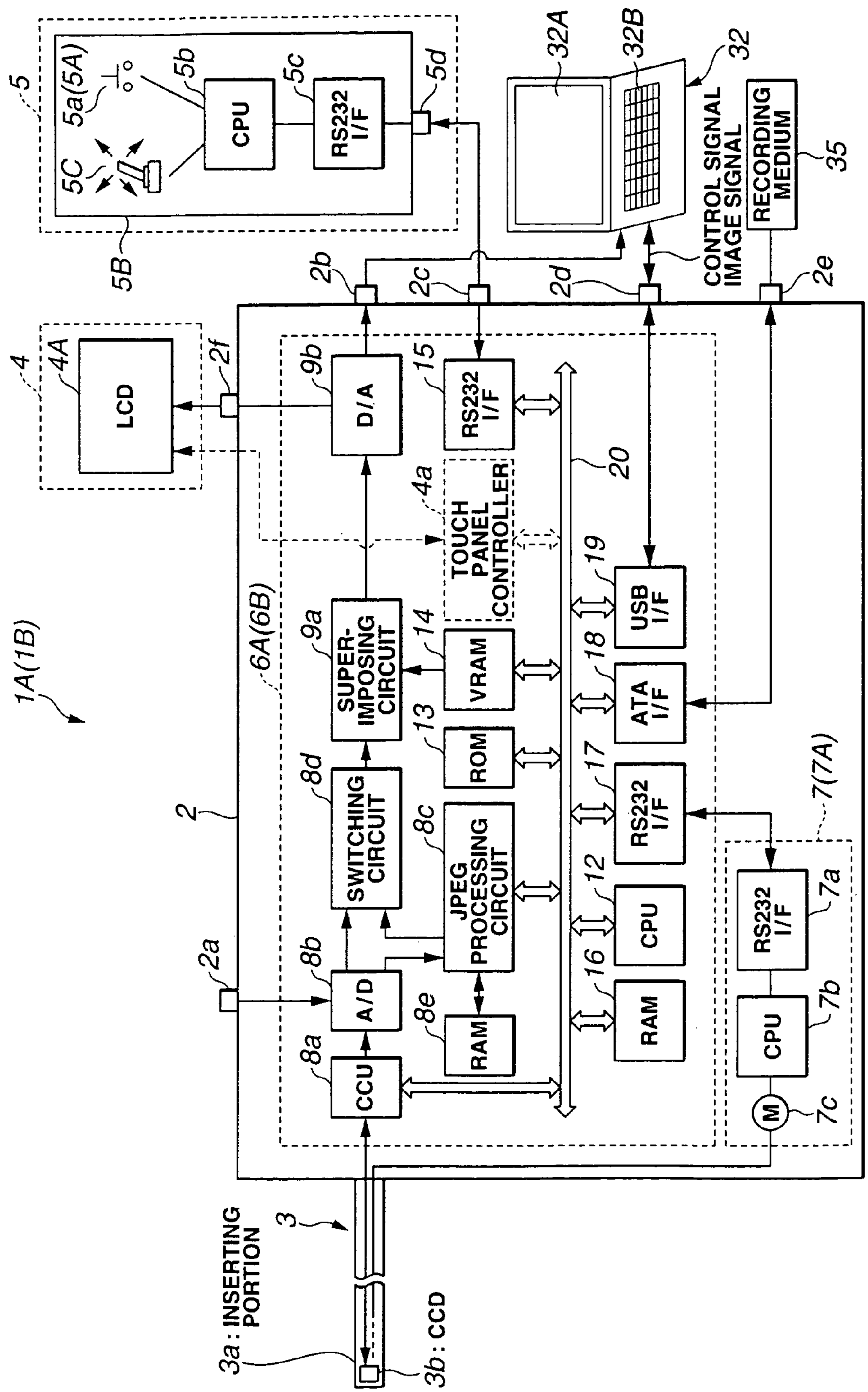
FIG. 14 is a block diagram showing a specific electric circuit structure of the endoscope device shown in FIG. 13A.

FIG. 14 shows the specific electric circuit structures of the endoscope devices 1A and 1B. The specific structures of the system control units 6A and 6B according to the second embodiment are the same as that according to the first embodiment.

The PC 32 serving as the feature according to the second embodiment is connected to the connecting terminal 2*d* of the device main body 2.

As mentioned above, the PC 32 comprises the rotating-image processing portion 9, the direction processing portion 11, and the direction calculation processing portion 10 which are arranged in the system control unit 6 according to the first embodiment, and performs the same control operation as that of the system control unit 6 according to the first embodiment.

Figure 15:
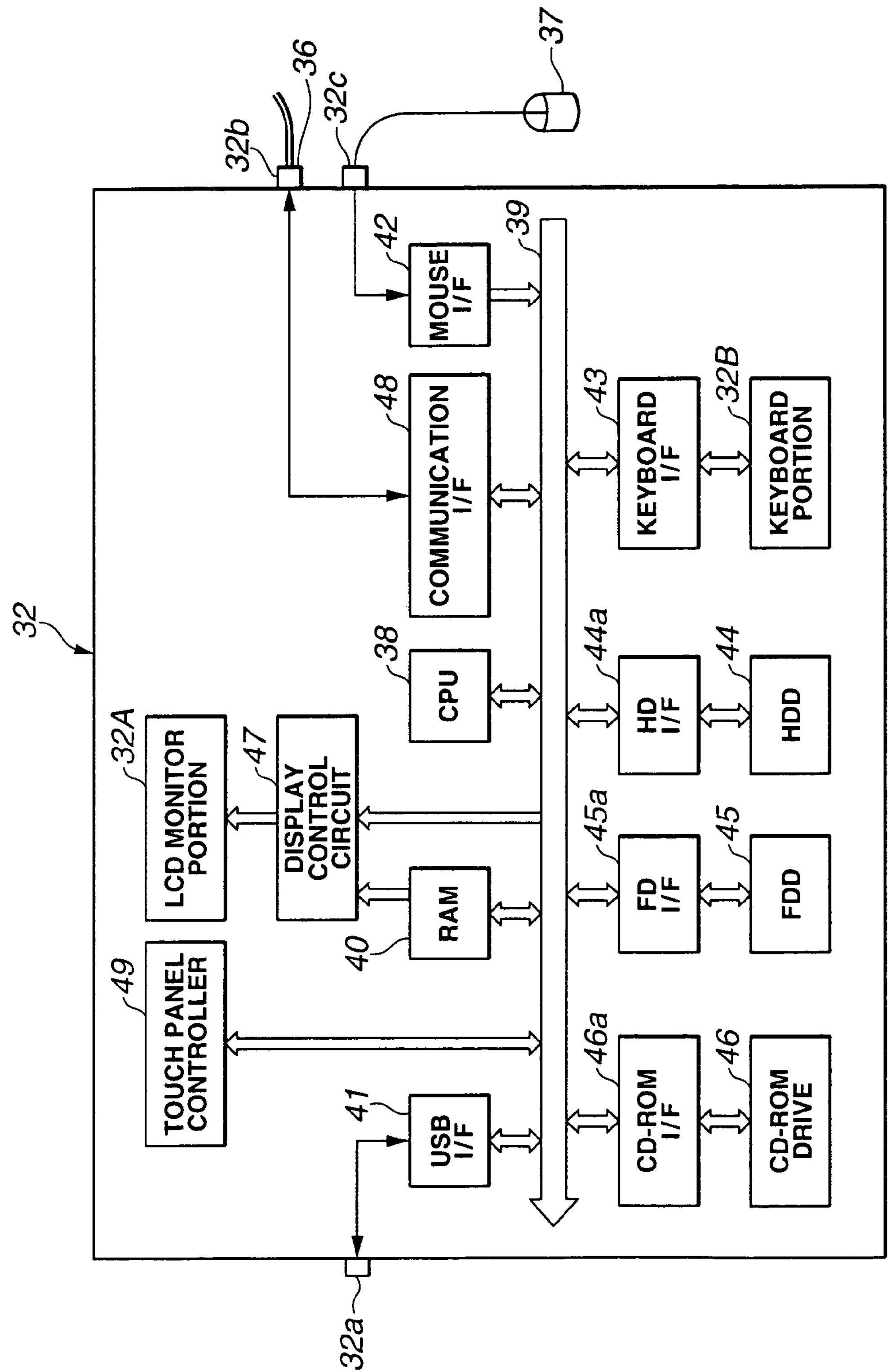
FIG. 15 is a block diagram showing a specific electric circuit structure of an endoscope control unit shown in FIG. 13B.

FIG. 15 shows the specific circuit structure of the PC 32.

The structure shown in FIG. 15 is not specific to the PC 32 according to the second embodiment and is of general PCs for examination that are commercially available. Further, a USB interface 41 and a USB connector receiver 32*a* are arranged to any types of PCs for examination that have been recently sold.

In the PC 32 serving as the endoscope control unit, a CPU 38 for entire control operation is connected to an internal bus 39. Connected to the internal bus 39 are a RAM 40 used as a work area of the CPU 38, a USB I/F 41 connected to a USB connector receiver 32*a,* and a mouse I/F 42 to which a connector of a mouse 37 is connected (via the connector receiver).

Connected to the internal bus 39 are a keyboard unit 32B, a hard disk (abbreviated to an HD in the drawing) drive 44 for storing a program, a flexible disk (abbreviated to an FD) 45 such as a floppy (registered trademark) disk, and a CD-ROM drive 46 via I/Fs 43, 44*a*, 45*a,* and 46*a.* A communication I/F 48 is connected to the internal bus 39, and the communication I/F 48 is connected to a communication line such as LAN or Internet via a cable 36.

An LCD monitor portion 32A is connected to the RAM 40 and the internal bus 39 via a display control circuit 47 for controlling the display operation.

The CPU 38 first reads the program included in the hard disk drive 44, writes the read program to a predetermined area of the RAM 40. Then, the CPU 38 is operated under the program. The hard disk stores the processing routine program shown in FIG. 10 and the determining area table shown in FIG. 8.

The CPU 38 prepares the image data for display on the screen at a predetermined area in the RAM 40. The display control circuit 47 repeatedly reads the image data for display on the screen, and always converts the read data into a signal for display on the monitor portion 32A. The signal is sent and is displayed on the monitor portion 32A.

The image data sent to the PC 32 from the endoscope 3 is received by the USB I/F 41, and is read by the CPU 38 via the internal bus 39. The CPU 38 restores the image data before compressing the image data in accordance with the program, and writes the restored data at a predetermined area of the RAM 40 to be displayed on the monitor portion 32A.

Figure 16B:
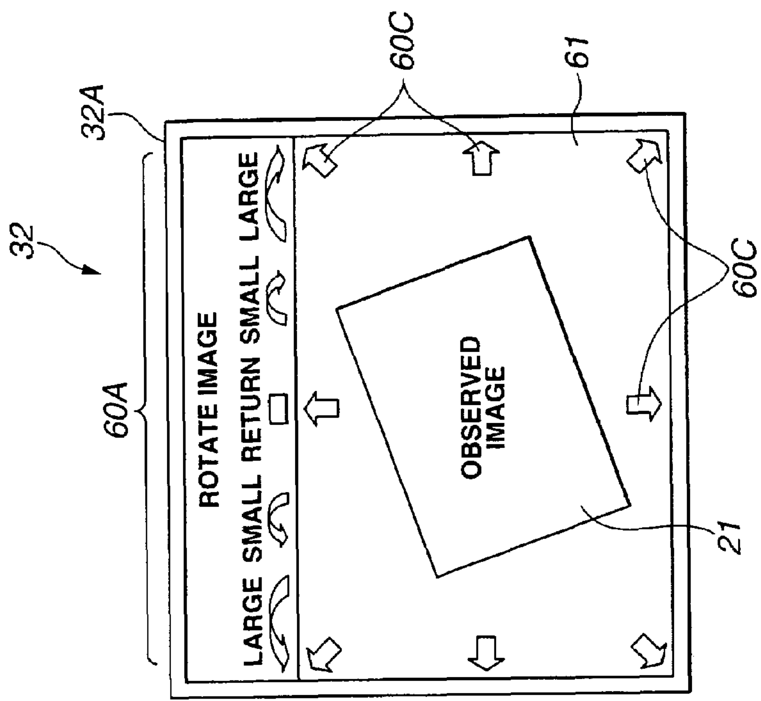
FIG. 16B is an explanatory diagram of a display screen showing another structure example of the bending-direction instructing portion.
Figure 16A:
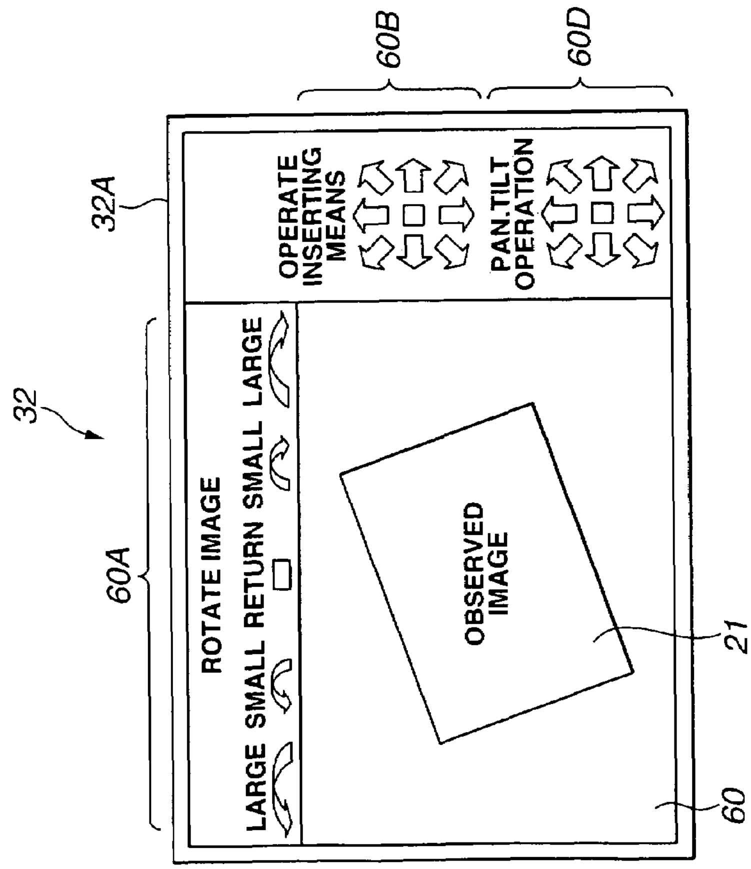
FIG. 16A is an explanatory diagram showing an example of a display screen of the endoscope control unit serving as the feature according to the second embodiment, further showing a display screen when a rotation-instructing display unit and a bending-direction instructing display unit.

According to the second embodiment, referring to FIG. 16, similarly to the first embodiment, the monitor screen of the monitor portion 32A displays: a screen 60 for displaying the endoscope image 21 picked-up by the CCD 3*b* of the endoscope 3; rotate instructing switches 60A for rotating the endoscope image 21; direction instructing portions 60B for controlling the bending the endoscope 3 or the like; and a direction instructing portion 60D for panning/tilting the image in the zoom operation.

The keyboard 32B or mouse 37 sets the movement of an operating cursor at the desired positions of various switches in the rotate instructing switches 60A and direction instructing portions 60B displayed on the monitor screen. The click operation of the mouse 37 operates the function of the clicked button.

The rotating switches 60A displayed on the monitor screen is the same as the large-rotate instructing switch 26, the small-rotate instructing switch 28, and the reference switch 27 arranged to the operating remote controller 5 according to the first embodiment. The direction instructing portions 60B for controlling the bending operation of the endoscope 3 comprise switches that instruct the operation in the upper left direction (UL direction), up direction (U direction), upper right direction (UR direction), left direction (L direction), right direction (R direction), down left direction (DL direction), down direction (D direction), and down right direction (DR) direction, and the center direction, similarly to the first embodiment.

A direction instructing portion 60D for panning/tilting operation of the image in the zoom operation comprise switches that instruct the operation in the upper left direction (UL direction), up direction (U direction), upper right direction (UR direction), left direction (L direction), right direction (R direction), down left direction (DL direction), down direction (D direction), and down right direction (DR) direction, and the center direction, similarly to the first embodiment.

Referring to FIG. 16(*b*), in order to simplify the operations of the direction instructing portions 60B and 60D for controlling the bending operation, a direction instructing portion 60C indicating various operating directions may be arranged in the corner of the screen 61 in accordance with the operating directions.

According to the second embodiment, the movement of the operating cursor is set at the desired positions of the switches in the direction instructing portions 60B, 60D, or 61, and the mouse 37 is clicked. Thus, the operation for instructing the bending direction and the PAN/TILT operation in the zoom operation are determined. However, the present invention is not limited to this. For example, the operation for instructing the bending direction and the PAN/TILT operation in the zoom operation may be determined only by setting the movement of the operating cursor at the desired positions of the switches. Consequently, the operating direction is easily instructed without any click operation or the like.

The operating signals from the rotate instructing switches 60A and the direction instructing portions 60B and 60D are inputted to the touch panel controller 49 shown in FIG. 15. The touch panel controller 49 converts the operating signals into the control signals and supplies the converted control signals to the CPU 38.

Similarly to the first embodiment, the CPU 38 controls an image pickup processing portion, direction calculation processing portion, and a rotating-image processing portion (which are not shown) based on the operating signals, thereby performing the image processing at the rotating angle based on the rotating instruction. Further, the CPU 38 displays the processed image on the screen 60 (61) of the monitor portion 32A, or obtains the operating directions of the direction instructing portions 60B, 60D, and 60C. In addition, the bending direction and the moving direction of the image are corrected based on the rotating angle of image by using the direction processing portion and the direction calculation processing portion. The driving operation of the driving unit 7 is controlled based on the correcting result, the PAN/TILT instruction is issued to the image pickup processing portion 8, the image is panned/tilted, and the image in the direction corresponding to the direction instructing portion of the operator is displayed on the screen 60 (61) of the monitor portion 32A.

Next, a description is given of an example of control operation serving as the feature of an endoscope device 1A (1B) according to the second embodiment.

The endoscope device 1A (1B) according to the second embodiment is operated similarly to the example of control operation (refer to FIG. 10) of the CPU 12 in the system control unit 6 described according to the first embodiment. However, the control operation is executed by the CPU 38 on the PC 32 side arranged as the endoscope control unit.

That is, the PC 32 displays the image processing based on the rotating instruction executed according to the first embodiment, controls the bending operation of the endoscope 3 based on the instruction of direction, and further controls the PAN/TILT operation and the display operation in the zoom operation. In this case, the processing of the CPU 38 is executed by using the determining area table (refer to FIG. 8) stored in the hard disk drive 44 or RAM 40.

The PC 32 may control the switching operation of the first switching portion 34*a* to display the display screen 60 (61) displayed on the monitor portion 32A of the PC 32 on the monitor 4A on the device main body 2 side.

Further, similarly to the system control unit 6 according to the first embodiment, the direction instructing portions 60B (60C or 60D) may be displayed on the screen of the monitor 4A on the device main body side. The operating signal based on the direction instructing portions 60B (60C or 60D) may be supplied to the CPU 12 via the touch panel controller 4*a* arranged in the system control unit 6A (6B). The CPU 12 may control the bending operation of the endoscope 3 or PAN/TILT the image in the zoom operation.

Therefore, according to the second embodiment, in the case of arranging the PC serving as the endoscope control unit connected to the device main body 2, the same operations as those according to the first embodiment are obtained. Thus, the endoscope image from the endoscope matches the viewing direction of the operator without any feeling of strangeness.

Figure 17:
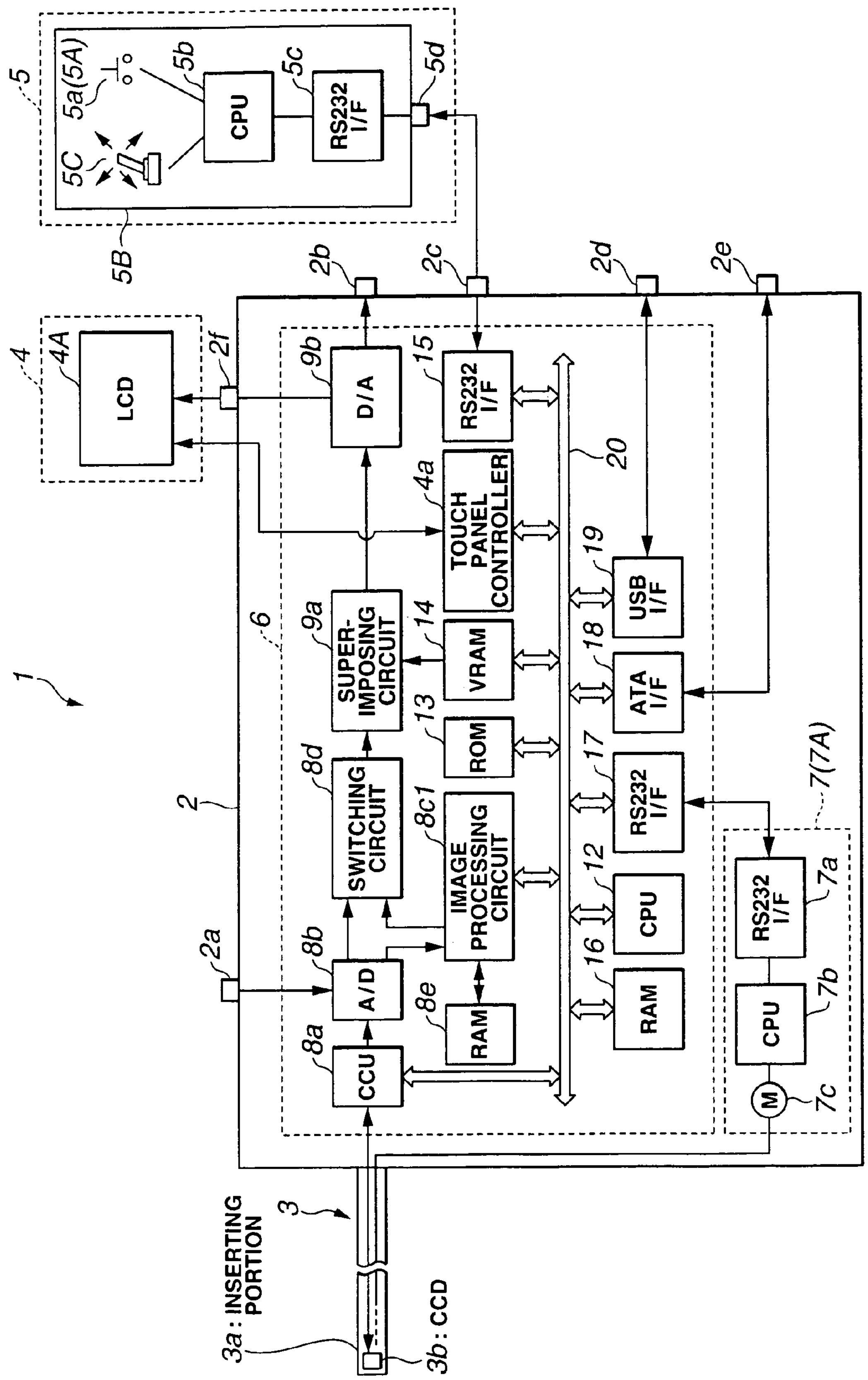
FIG. 17 is a block diagram showing a specific electric circuit structure of an endoscope device according to a third embodiment of the present invention.

FIG. 17 is a block diagram showing the electric circuit structure of an endoscope device according to a third embodiment. Referring to FIG. 17, the same components as those shown in FIG. 2 according to the first embodiment are designated by the same reference numerals, and a description thereof is omitted.

Referring to FIG. 17, the endoscope device according to the third embodiment uses an image processing circuit 8*c*1, in place of the JPEG processing circuit 8*c* in the structure shown in FIG. 2 according to the first embodiment.

When the CPU 12 sets the compression processing mode, the image processing circuit 8*c*1 encodes the supplied digital image data, compresses the data, and outputs the compressed data to the bus 20.

Alternatively, when the CPU 12 sets a decompression processing mode, the image processing circuit 8*c*1 complexes the compressed image date read from an image recording medium (not shown) connected to the terminal 2*e* via the ATA I/F 18, and outputs the processed data to the switching circuit-8*d*.

In this case, the CPU 12 executes the processing of the image processing circuit 8*c*1 on the work area of the RAM 8*e*. The compressed image data is temporarily stored in the RAM 16 via the bus 20. The CPU 12 controls the recording and reading operation of the image data to/from the RAM 16. The operating remote controller records the image data to an external image recording medium (not shown) via the ATA I/F 18.

When the CPU 12 sets a non-compression processing mode, the image processing circuit 8*c*1 outputs the supplied digital image data without any compression, and outputs, to the switching circuit 8*d*, non-compressed image data read from the image recording medium (not shown) connected to the terminal 2*e* via the ATA I/F 18.

The image processing circuit 8*c*1 receives the designated angle for rotating the image from the CPU 12, rotates the image on the work area of the RAM 8*e*, and outputs, to the bus 20, the compressed image data and non-compressed image data in accordance with the compression processing mode/non-compression processing mode of the CPU 12. The image processing circuit 8*c*1 outputs, to the switching circuit 8*d*, the image data that is subjected to the image rotation by the setting from the CPU 12. In this case, the image processing circuit 8*c*1 outputs the non-compressed image data, irrespective of the compressing mode/non-compressing mode.

The CPU 12 rotates the image data obtained via the bus 20 from the image processing circuit 8*c*1 in the RAM 16, outputs the processed data to the image processing circuit 8*c*1, and outputs it to the switching circuit 8*d*.

The CPU 12 rotates the image data obtained via the bus 20 from the image processing circuit 8*c*1 in the RAM 16, and outputs the image data to the VRAM 14.

Other structures are the same as those according to the first embodiment.

According to the third embodiment, the same operations and advantages as those according to the first embodiment are obtained when the JPEG processing circuit 8*c* is changed to the image processing circuit 8*c*1.

Figure 18:
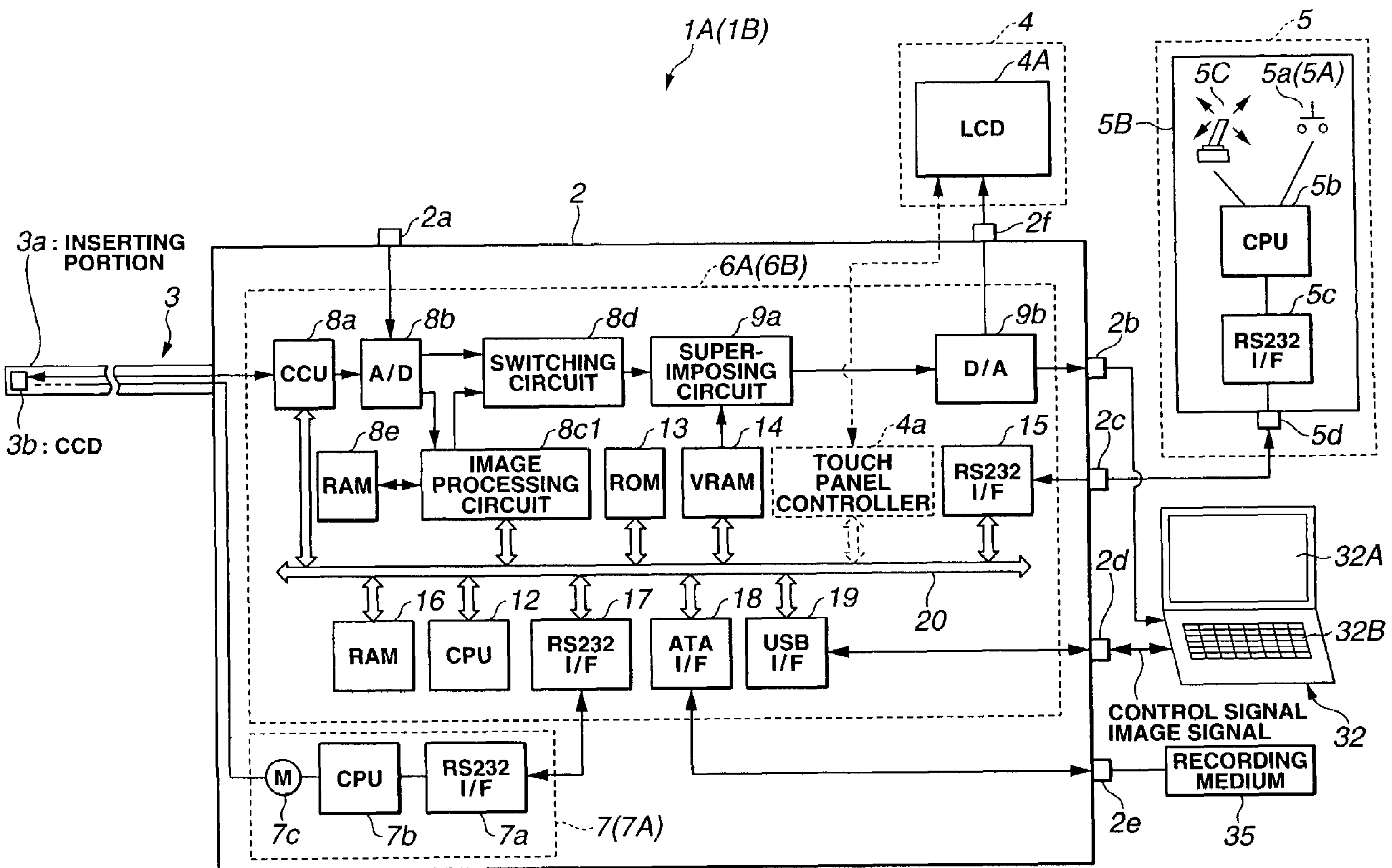
FIG. 18 is a block diagram showing a specific electric circuit structure of an endoscope device according to a fourth embodiment of the present invention.

FIG. 18 is a block diagram showing a specific electric circuit structure of an endoscope device according to a fourth embodiment of the present invention. Referring to FIG. 18, the same components shown in FIG. 14 according to the second embodiment are designated by the same reference numerals, and a description thereof is omitted.

Referring to FIG. 18, the endoscope device according to the fourth embodiment uses the image processing circuit 8*c*1, in place of the JPEG processing circuit 8*c* in the structure shown in FIG. 14 according to the second embodiment.

Further, the endoscope device 1A (1B) according to the fourth embodiment shown in FIG. 18 is the same as the endoscope device 1 shown in FIG. 17 according to the third embodiment, and a description thereof is omitted.

Other structures are the same as those according to the second embodiment.

According to the forth embodiment, the same operations and advantages as those according to the second embodiment are obtained when the JPEG processing circuit 8*c* is changed to the image processing circuit 8*c*1.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope device comprising:

an endoscope that can be inserted to a portion to be observed and has an inserting portion having image pickup means at the distal-end side thereof that obtains an observed image;

an image pickup processing portion that converts the observed image of the endoscope into an image signal that can be displayed on a display unit;

a direction instructing portion that instructs a moving direction of a display image displayed on the display unit;

a direction calculation processing portion that processes the amount of movement of the display image in accordance with an instruction from the direction instructing portion; and a rotation instructing portion that instructs the rotation of the display image of the display unit at an arbitrary angle, wherein the direction calculation processing portion corrects a moving direction of the display image based on an instruction of the rotation instructing portion.

2. An endoscope device according to claim 1, further comprising:

an image processing control unit that controls the image pickup processing portion based on a processed result of the direction calculation processing portion.

3. An endoscope device according to claim 2, further comprising:

a rotating-image processing portion that performs rotating-image processing of the observed image displayed on the display unit based on the instruction from the rotation instructing portion.

4. An endoscope device according to claim 3, wherein the rotating-image processing portion processes the image size to arbitrarily be changed so as to include the entire display image subjected to the rotating-image processing on a display screen of the display unit.

5. An endoscope device according to claim 2, wherein the direction instructing portion and the direction calculation processing portion are arranged in an endoscope control unit connected to the endoscope by communication means.

6. An endoscope device according to claim 1, further comprising:

a rotating-image processing portion that performs rotating-image processing of the observed image displayed on the display unit based on the instruction from the rotation instructing portion.

7. An endoscope device according to claim 6, wherein the rotating-image processing portion processes the image size to arbitrarily be changed so as to include the entire display image subjected to the rotating-image processing on a display screen of the display unit.

8. An endoscope device according to claim 1, wherein the direction instructing portion and the direction calculation processing portion are arranged in an endoscope control unit connected to the endoscope by communication means.

9. An endoscope device according to claim 8, wherein the endoscope control unit is a personal computer.

10. An endoscope device comprising:

an endoscope that can be inserted to a portion to be observed and has an inserting portion having image pickup means at the distal-end side thereof that obtains an observed image;

an image pickup processing portion that converts the observed image of the endoscope into an image signal that can be displayed on a display unit;

a direction instructing portion that instructs a processing of a bending direction of the inserting portion;

a direction calculation processing portion that processes the bending direction of the inserting portion in accordance with an instruction from the direction instructing portion;

a rotation instructing portion that instructs the rotation of the display image of the display unit at an arbitrary angle; and a driving control unit that controls the operation of the inserting portion of the endoscope based on a processed result of the direction calculation processing portion;

wherein the direction calculation processing portion corrects a bending direction of the inserting portion of the endoscope based on an instruction of the rotation instructing portion.

11. An endoscope device according to claim 10, further comprising:

a rotating-image processing portion that performs rotating-image processing of the observed image displayed on the display unit based on the instruction from the rotation instructing portion.

12. An endoscope device according to claim 11, wherein the rotating-image processing portion processes the image size to arbitrarily be changed so as to include the entire display image subjected to the rotating-image processing on a display screen of the display unit.

13. An endoscope device according to claim 10, wherein the direction instructing portion and the direction calculation processing portion are arranged in an endoscope control unit connected to the endoscope by communication means.

14. An endoscope device comprising:

an image pickup processing portion that converts an observed image obtained by image pickup means of an endoscope inserted to a portion to be observed, into an image signal that can be displayed on a display unit;

a direction instructing portion that instructs a moving direction of a display image displayed on the display unit;

a direction calculation processing portion that processes the amount of movement of the display image in accordance with an instruction from the direction instructing portion; and a rotation instructing portion that instructs the rotation of the display image of the display unit at an arbitrary angle, wherein the direction calculation processing portion corrects a moving direction of the display image based on an instruction of the rotation instructing portion.

15. An endoscope device endoscope device according to claim 14, further comprising:

a driving control unit that controls the operation of the inserting portion of the endoscope based on a processed result of the direction calculation processing portion.

16. An endoscope device according to claim 14, further comprising:

an image processing control unit that controls the image pickup processing portion based on a processed result of the direction calculation processing portion.

* * * * *